United States Patent
Van Schalkwyk et al.

(10) Patent No.: US 12,268,816 B2
(45) Date of Patent: Apr. 8, 2025

(54) BREATHING ASSISTANCE APPARATUS

(71) Applicant: Fisher & Paykel Healthcare Limited, Auckland (NZ)

(72) Inventors: Andre Van Schalkwyk, Auckland (NZ); Andrew Paul Maxwell Salmon, Auckland (NZ); Ramirlindo Agra Dawinan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 954 days.

(21) Appl. No.: 17/309,189

(22) PCT Filed: Nov. 5, 2019

(86) PCT No.: PCT/IB2019/059462
§ 371 (c)(1),
(2) Date: May 4, 2021

(87) PCT Pub. No.: WO2020/095185
PCT Pub. Date: May 14, 2020

(65) Prior Publication Data
US 2021/0370014 A1 Dec. 2, 2021

Related U.S. Application Data

(60) Provisional application No. 62/755,928, filed on Nov. 5, 2018.

(51) Int. Cl.
*A61M 16/16* (2006.01)
*A61M 16/06* (2006.01)
*A61M 16/10* (2006.01)

(52) U.S. Cl.
CPC ........ *A61M 16/16* (2013.01); *A61M 16/0666* (2013.01); *A61M 16/109* (2014.02)

(58) Field of Classification Search
CPC .. A61M 16/14; A61M 16/142; A61M 16/147; A61M 16/16; A61M 16/161;
(Continued)

(56) References Cited

U.S. PATENT DOCUMENTS 6,256,454 B1 * 7/2001 Dykes .................... A61G 11/00
392/403
7,327,949 B1 2/2008 Cheng
(Continued)

FOREIGN PATENT DOCUMENTS

JP 2015-514541 5/2015
JP 2018-518297 7/2018
(Continued)

OTHER PUBLICATIONS

International Search Report for International Application No. PCT/IB2019/059462 dated Feb. 3, 2020.

*Primary Examiner* — Kendra D Carter
*Assistant Examiner* — Jaeick Jang
(74) *Attorney, Agent, or Firm* — VIA LLP

(57) ABSTRACT

A breathing assistance apparatus has a housing with a recess. A guard is mounted to the housing, the guard having a base and a barrier. At least part of the base is flexible. The barrier is movable between a covering position in which the barrier partly covers the recess and an access position in which the recess is less covered or is uncovered by the barrier. Said at least part of the base is configured to flex as the barrier is moved between the covering position and the access position.

18 Claims, 18 Drawing Sheets

(58) Field of Classification Search
CPC .............. A61M 16/162; A61M 16/164; A61M 16/165; A61M 16/167; A61M 16/168; A61M 16/18; A61M 16/186; A61M 16/1075; A61M 16/108; A61M 16/1085; A61M 16/109; A61M 2205/3368; A61M 2205/505; A61M 2205/3379; A61M 2205/3382; A61M 2205/3386; A61M 2205/3389; A61M 2205/3393; A61M 2205/3396; A61M 2209/04; A61M 2209/045; F24F 6/00; F24F 6/08; F24F 2006/008; A61D 7/04; A62B 9/003; H05B 1/0269; H05B 2203/021
See application file for complete search history.

(56) References Cited

U.S. PATENT DOCUMENTS

| | | | |
|---|---|---|---|
| 2003/0066526 A1* | 4/2003 | Thudor | A61M 16/161 128/203.26 |
| 2003/0196656 A1 | 10/2003 | Moore et al. | |
| 2008/0178886 A1 | 7/2008 | Lieberman et al. | |
| 2008/0302361 A1 | 12/2008 | Snow et al. | |
| 2009/0194106 A1 | 8/2009 | Smith et al. | |
| 2017/0151411 A1 | 6/2017 | Osborne et al. | |
| 2017/0361051 A1 | 12/2017 | Eifler | |
| 2021/0379322 A1* | 12/2021 | Maurer | A61M 16/16 |

FOREIGN PATENT DOCUMENTS

| | | |
|---|---|---|
| WO | WO 2007/038152 | 4/2007 |
| WO | WO 2009/011907 A1 | 1/2009 |
| WO | WO 2011/056080 | 5/2011 |
| WO | 2013045586 A1 | 4/2013 |
| WO | 2014138804 A1 | 9/2014 |
| WO | WO 2015/038013 | 3/2015 |
| WO | WO 2016/089224 A1 | 6/2016 |
| WO | WO 2016/097928 | 6/2016 |
| WO | WO 2016/207838 | 12/2016 |
| WO | WO 2018/199774 A1 | 11/2018 |

* cited by examiner

BREATHING ASSISTANCE APPARATUS

TECHNICAL FIELD

The present invention relates to a breathing assistance apparatus.

BACKGROUND ART

Breathing assistance apparatuses are used in various environments such as hospital, medical facility, residential care, or home environments to deliver a flow of gas to users or patients. The breathing assistance apparatuses come in various forms, such as a standalone humidifier apparatus, a continuous positive airway pressure (CPAP) apparatus, a high flow apparatus, or a ventilator.

A standalone humidifier apparatus can deliver heated and humidified gases for various medical procedures, including respiratory therapy, laparoscopy, and the like. These apparatuses can be configured to control temperature and/or humidity. The apparatuses can &so include medical circuits comprising various components that can be used to transport heated and/or humidified gases to and from patients. For example, in some breathing circuits, gases inhaled by a patient are delivered from a heater-humidifier through an inspiratory tube or conduit. As another example, tubes can deliver humidified gas (commonly $CO_2$) into the abdominal cavity in insufflation circuits. This can help prevent desiccation or 'drying out' of the patient's internal organs, and can decrease the amount of time needed for recovery from surgery. Heater wires may extend inside of at least a portion of the tubing forming the circuit to prevent or at least reduce the likelihood of the formation of significant condensation.

A standalone humidifier apparatus would typically include a heater base and a humidification liquid chamber. The heater base can comprise a heater plate. The liquid chamber can be configured to hold a volume of a liquid, such as water. The heater plate can be configured to heat the volume of liquid held within the liquid chamber to produce vapour.

The liquid chamber is removable from the heater base to allow the liquid chamber to be more readily sterilized or disposed, or to re-fill the chamber with liquid. The body of the liquid chamber can be formed from a non-conductive glass, or plastics material but the liquid chamber can also include conductive components. For instance, the liquid chamber can include a highly heat-conductive base (for example, an aluminum base) contacting or associated with the heater plate on the heater base.

The heater base can also include electronic controls such as a master controller. In response to user-set humidity or temperature values input via a user interface and other inputs, the master controller determines when (or to what level) to energize the heater plate to heat the liquid within the liquid chamber.

The standalone humidifier apparatus can include a gases supply to deliver gases to the liquid chamber. in some configurations, the oases supply can comprise a ventilator, blower, or any other suitable source of pressurized oases suitable for breathing or use in medical procedures.

A standalone humidifier apparatus can be used with breathing therapies, positive pressure apparatus, noninvasive ventilation, surgical procedures including but not limited to laparoscopy, and the like. Desirably, the humidifier apparatus can be adapted to supply humidity or vapour to a supply of gases. The humidifier apparatus can be used with continuous, variable, or bi-level PAP systems or other form of respiratory therapy. In some configurations, the humidifier apparatus can be integrated into a system that delivers any such types of therapy.

An exemplary standalone humidifier apparatus is described in WO 2015/038013.

A CPAP apparatus is a gases supply and optionally gases humidification apparatus. The apparatus is operable to provide respiratory assistance to patients or users who require a supply of gas (humidified or otherwise) at positive pressure for the treatment of diseases such as Obstructive Sleep Apnea (OSA), snoring, or Chronic Obstructive Pulmonary Disease (COPD) and the like. A CPAP apparatus would typically include a humidification liquid chamber, so as to form a combined assisted breathing unit and humidifier.

CPAP apparatuses, when used with a humidifier, typically have a structure where gases at a required pressure are delivered from an assisted breathing unit or blower unit to a liquid chamber downstream from the blower. As the gases pass through the liquid chamber, they become saturated with liquid vapour (e.g. water vapour). A flexible tubular gases conduit delivers the gases to a user or patient downstream from the humidifier chamber.

An exemplary CPAP apparatus is described in WO 2011/056080.

A high flow apparatus may be used to deliver a high gas flow or high flow therapy to a patient to assist with breathing and/or treat breathing disorders including chronic obstructive pulmonary disease (COPD). A high flow apparatus includes a gases supply and typically includes a humidification apparatus.

The breathing assistance apparatuses typically have one or more accessories such as a breathing conduit and a patient interface such as a cannula or mask for delivering gases to a patient. The conduit enables gases to be delivered from the housing of the breathing assistance apparatus to the patient. For example, the apparatus may be placed on a floor or other support surface, and the patient may be in a bed. The breathing assistance apparatus may have a recess for receipt of a humidifier liquid chamber. The liquid chamber will receive liquid from, for example, a flexible liquid bag that delivers liquid to a humidifier liquid chamber via one more tubes. Alternatively, the liquid chamber can be removed and refilled as required. The recess will contain a heater plate to heat the liquid chamber, to humidify gases passing through the liquid chamber. The humidified gases are then delivered to the patient.

SUMMARY

In accordance with certain features, aspects and advantages of at least one of the embodiments disclosed herein, a breathing assistance apparatus is disclosed, the breathing assistance apparatus comprising: a housing with a recess; and a guard mounted to the housing, the guard comprising a base and a barrier, at least part of the base being flexible, the barrier being movable between a covering position in which the barrier partly covers the recess and an access position in which the recess is less covered or is uncovered by the barrier, and wherein said at least part of the base is configured to flex as the barrier is moved between the covering position and the access position In some configurations, the base of the guard is mounted to a base of the housing.

In some configurations, the base of the guard is mounted to the base of the housing by one or more fasteners.

In some configurations, the guard is fastened to the exterior of the housing and is replaceable without disassembling the housing.

In some configurations, the barrier is configured to act as a bumper.

In some configurations, the base of the guard is configured so that the barrier can substantially only move in two opposed directions by flexing the base of the guard, and so that the barrier cannot substantially move in other directions by flexing the base of the guard, even if a single region of the barrier is pushed by a user.

In some configurations, the guard is configured so that it cannot twist about an axis that extends in a forward-rearward direction along the base and through the barrier of the guard.

In some configurations, the breathing assistance apparatus comprises a heater plate in the recess and the recess is configured to removably receive a liquid chamber, wherein the guard shields a base of the liquid chamber from contact by a user when the barrier is in the covering position and the liquid chamber is in the recess.

In some configurations, the base of the liquid chamber comprises a base flange, and the guard shields the base flange from contact by a user when the barrier is in the covering position and the liquid chamber is in the recess.

In some configurations, the recess is configured to removably receive a liquid chamber, and the barrier blocks insertion or removal of a liquid chamber into or from the recess, in the absence of flexing of the base of the guard.

In some configurations, the base of the guard can be flexed by pushing on the barrier.

In some configurations, the base of the guard can be flexed by moving the liquid chamber in a removal direction from the recess.

In some configurations, the barrier is configured such that contact between the liquid chamber and a contact surface of the barrier as the liquid chamber is moved in the removal direction, moves the barrier from the covering position to the access position.

In some configurations, the contact surface of the barrier is at a non-perpendicular angle of more than 90 degrees and less than 180 degrees relative to the removal direction, optionally between 100 degrees and 170 degrees relative to the removal direction, optionally between 110 degrees and 135 degrees relative to the removal direction, optionally between 120 degrees and 130 degrees relative to the removal direction, and optionally 125 degrees relative to the removal direction.

In some configurations, the barrier is configured so that the base of the guard cannot be flexed by moving the liquid chamber in a removal direction from the recess.

In some configurations, the barrier is configured such that contact between the liquid chamber and a contact surface of the barrier in a removal direction of the liquid chamber, will not cause the barrier to move away from the covering position.

In some configurations, the contact surface is at an angle of about 90 degrees or less relative to the removal direction of the liquid chamber.

In some configurations, the barrier is biased to the covering position.

In some configurations, one or more biasing devices act between the housing and the guard to bias the barrier to the covering position.

In some configurations, the one or more biasing devices act between the housing and the barrier.

In some configurations, said at least part of the base of the guard is resiliently flexible, to bias the barrier to the covering position.

In some configurations, the base of the guard comprises one or more drainage ports or drainage spaces to allow liquid to drain through or around the base of the guard.

In some configurations, the housing comprises a projection and the base of the guard comprises a complementary aperture to receive the projection to resist horizontal movement of the base of the guard.

In some configurations, the guard is integrally formed with the housing or is fastened to the housing.

Additionally, in accordance with certain features, aspects and advantages of at least one of the embodiments disclosed herein, a breathing assistance apparatus is disclosed, the breathing assistance apparatus comprising: a housing with a recess configured to removably receive a liquid chamber; and a guard comprising a barrier, the barrier being movable between a covering position in which the barrier partly covers the recess and overlaps part of the liquid chamber when the liquid chamber is in the recess, and an access position in which the recess is less covered or is uncovered by the barrier and the barrier exposes the part of the liquid chamber, wherein the barrier is biased to the covering position, and wherein the barrier is configured to move from the covering position to the access position by moving the liquid chamber in a removal direction from the recess.

In some configurations, the barrier is configured such that contact between the liquid chamber and a contact surface of the barrier as the liquid chamber is moved in the removal direction, moves the barrier from the covering position to the access position.

In some configurations, the contact surface of the barrier is at a non-perpendicular angle of more than 90 degrees and less than 180 degrees relative to the removal direction, optionally between 100 degrees and 170 degrees relative to the removal direction, optionally between 110 degrees and 135 degrees relative to the removal direction, optionally between 120 degrees and 130 degrees relative to the removal direction, and optionally 125 degrees relative to the removal direction.

In some configurations, said part of the liquid chamber comprises a front edge of a base flange of the liquid chamber, and the contact surface is configured to contact substantially the entire front edge of the base flange as the liquid chamber is moved in the removal direction.

In some configurations, the recess comprises a liquid chamber retention guide rail, and wherein the liquid chamber retention guide rail is forwardly open to enable the liquid chamber to be inserted into the recess with a back and sides of the base flange under the guide rail and with the front edge of the base flange exposed from the guide rail.

In some configurations, the contact surface has a constant angle throughout a contact area between the liquid chamber and the barrier, when viewed in side projection.

In some configurations, one or more biasing devices act between the housing and the guard to bias the barrier to the covering position.

In some configurations, the one or more biasing devices act between the housing and the barrier.

In some configurations, the barrier is linearly movable between the covering position and the access position.

In some configurations, part of the guard is resiliently flexible, to bias the barrier to the covering position.

In some configurations, the guard is integrally formed with the housing or is fastened to the housing.

Additionally, in accordance with certain features, aspects and advantages of at least one of the embodiments disclosed herein, a breathing assistance apparatus is disclosed, the breathing assistance apparatus comprising: a housing with a recess; and a guard mounted to the housing, the guard comprising a barrier that is movable between a covering position in which the barrier partly covers the recess and an access position in which the recess is less covered or is uncovered by the barrier, wherein the guard is fastened to an exterior of the housing and is replaceable without disassembling the housing.

In some configurations, the barrier is configured to act as a bumper.

In some configurations, the guard covers a front exterior part of the recess.

In some configurations, the guard is fastened to a base of the housing.

In some configurations, the guard can be removed from the housing by removing fastener(s).

In some configurations, the guard has a colour that is representative of the intended function of the breathing assistance apparatus.

In some configurations, the recess is configured to removably receive a liquid chamber.

Additionally, in accordance with certain features, aspects and advantages of at least one of the embodiments disclosed herein, a breathing assistance apparatus is disclosed, the breathing assistance apparatus comprising: a housing with a gas port and a recess that is configured to removably receive a liquid chamber having a base flange with a back, sides, and front edge, the recess configured to removably receive the liquid chamber by moving the liquid chamber in a rearward insertion direction into the recess, with the back of the base flange inserted first; and a guard comprising a barrier, the barrier being movable between a covering position in which the barrier partly covers the recess and overlaps the front edge of the base flange of the liquid chamber when the liquid chamber is in the recess, and an access position in which the recess is less covered or is uncovered by the barrier and the barrier exposes the front edge of the base flange, the barrier comprising a transversely extending body portion and two upstanding portions at or adjacent respective sides of the transversely extending body portion.

In some configurations, the base flange has a substantially circular peripheral shape.

In some configurations, the breathing assistance apparatus comprises a heater plate in the recess, wherein the guard shields the base flange of the liquid chamber from contact by a user.

In some configurations, the barrier blocks insertion or removal of a liquid chamber into or from the recess when the barrier is in the covering position.

In some configurations, the barrier is biased to the covering position.

In some configurations, one or more biasing devices act between the housing and the guard to bias the barrier to the covering position.

In some configurations, the one or more biasing devices act between the housing and the barrier.

In some configurations, part of the guard is resiliently flexible, to bias the barrier to the covering position.

In some configurations, in the covering position the barrier is raised relative to the housing, and in the access position the barrier is lowered relative to the housing.

In some configurations, the barrier can be moved into the access position by actuating the guard.

In some configurations, the guard is configured to be actuated by pressing downwardly on the barrier.

In some configurations, each upstanding portion comprises an enlarged upper finger contact region for a user to press on to actuate the guard.

In some configurations, each upstanding portion comprises a narrow section beneath the upper finger contact region to accommodate a base of a liquid chamber when the guard is in the access position.

In some configurations, the guard comprises a base that is mounted to the housing, wherein the barrier extends from the base of the guard at a location that is distal to the mounting of the base to the housing.

In some configurations, at least part of the base is flexible, wherein said at least part of the base is configured to flex as the guard moves.

In some configurations, the base of the guard is configured so that the barrier can substantially only move in two opposed directions by flexing the base of the guard, and so that the barrier cannot substantially move in other directions by flexing the base of the guard, even if a single region of the barrier is pushed by a user.

In some configurations, the guard is configured so that it cannot twist about an axis that extends in a forward-rearward direction along the base and through the barrier of the guard.

In some configurations, surfaces of the upstanding portions are configured to interact with support portions of the housing during movement of the guard, to inhibit binding of the guard.

In some configurations, the support portions comprise extension members, and the surfaces of the upstanding portions are configured to slide against the extension members during at least part of the movement of the guard.

In some configurations, the surfaces are substantially vertical surfaces.

In some configurations, the guard is integrally formed with the housing or is fastened to the housing.

In some configurations, the recess comprises a liquid chamber retention guide rail, wherein the liquid chamber retention guide rail is forwardly open to enable the liquid chamber to be inserted into the recess with the back and sides of the base flange under the guide rail and with the front edge of the base flange exposed from the guide rail.

In some configurations, the housing is a main housing of the breathing assistance apparatus.

In some configurations, the gas port is an outlet port, and the housing comprises a motor recess, wherein a motor module is received in the motor recess to deliver gases to the liquid chamber via the outlet port.

In some configurations, the gas port is an inlet port and is configured to couple to a gas outlet port of the liquid chamber In some configurations, the housing further comprises an outlet port to deliver gases from the liquid chamber to a patient conduit.

Additionally, in accordance with certain features, aspects and advantages of at least one of the embodiments disclosed herein, a breathing assistance apparatus is disclosed, the breathing assistance apparatus comprising: a housing with a recess; and a guard mounted to the housing, the guard comprising a base and a barrier, the barrier comprising a transversely extending body portion and an upstanding portion at or adjacent a side of the transversely extending body portion, at least part of the base being flexible, the barrier being movable by a user applying force to the upstanding portion, between a covering position in which the barrier partly covers the recess and an access position in which the recess is less covered or is uncovered by the barrier, wherein said at least part of the base is configured to flex as the barrier is moved between the covering position and the access position, wherein the base is configured so that the barrier can substantially only move in two opposed directions between the covering position and the access position by flexing the base of the guard, and so that the barrier cannot substantially move in other directions by flexing the base of the guard, even if a single region of the barrier is pushed by a user.

In some configurations, the guard is configured so that it cannot twist about an axis that extends in a forward-rearward direction along the base and through the barrier of the guard.

In some configurations, a surface of the upstanding portion is configured to interact with a support portion of the housing during movement of the guard, to inhibit binding of the guard.

In some configurations, the support portion comprises an extension member, and wherein the surface of the upstanding portion is configured to slide against the extension member during at least part of the movement of the guard.

In some configurations, the surface is a substantially vertical surface.

In some configurations, the barrier comprises another upstanding portion at or adjacent an opposite side of the transversely extending body portion.

In some configurations, surfaces of the upstanding portions are configured to interact with support portions of the housing during movement of the guard, to inhibit binding of the guard.

In some configurations, the support portions comprise extension members, and wherein the surfaces of the upstanding portions are configured to slide against the extension members during at least part of the movement of the guard.

In some configurations, the surfaces are substantially vertical surfaces.

In some configurations, the base is mounted to the housing, and wherein the barrier extends from the base at a location that is distal to the mounting of the base to the housing.

In some configurations, the breathing assistance apparatus comprises a heater plate in the recess and the recess is configured to removably receive a liquid chamber, wherein the guard shields the base of the liquid chamber from contact by a user when the barrier is in the covering position and the liquid chamber is in the recess.

In some configurations, the recess is configured to removably receive a liquid chamber, and wherein the barrier blocks insertion or removal of a liquid chamber into or from the recess, in the absence of flexing of the base of the guard.

In some configurations, the base of the guard can be flexed by moving the liquid chamber in a removal direction from the recess.

In some configurations, the guard is integrally formed with the housing or is fastened to the housing.

In some configurations, the guard is fastened to the housing by at least two spaced apart fasteners.

Additionally, in accordance with certain features, aspects and advantages of at least one of the embodiments disclosed herein, a breathing assistance apparatus is disclosed, the breathing assistance apparatus comprising: a housing with a recess, wherein the housing comprises an outer surface having a first colour, the housing having a portion having a second colour that differs from the first colour; and a guard mounted to the housing and having a colour that differs from the second colour, the guard comprising a barrier that is movable between a covering position in which the barrier partly covers the recess and an access position in which the recess is less covered or is uncovered by the barrier, wherein the barrier is configured to cover the portion having a second colour when the barrier is in the covering position so that the portion having a second colour is not visible from an exterior of the apparatus, and wherein the barrier is configured to expose the portion having a second colour when the barrier is not in the covering position, so that the portion having a second colour is visible from an exterior of the apparatus when the barrier is not in the covering position.

In some configurations, the guard has a third colour that differs from the first colour and the second colour.

In some configurations, the portion having a second colour comprises an extension member that is positioned behind and/or below a portion of the barrier when the barrier is in the covering position.

In some configurations, the barrier comprises a transversely extending body portion and an upstanding portion at or adjacent a side of the transversely extending body portion, wherein the extension member is positioned behind and/or below the upstanding portion when the barrier is in the covering position, and wherein the extension member is exposed by the upstanding portion when the barrier is not in the covering position.

In some configurations, the barrier comprises a further upstanding portion at or adjacent an opposite side of the transversely extending body portion, wherein the housing comprises a further extension member having a second colour, and wherein the further extension member is positioned behind and/or below the further upstanding portion when the barrier is in the covering position, and wherein the further extension member is exposed by the further upstanding portion when the barrier is not in the covering position.

In some configurations, the portion having a second colour is visible from above and/or from a side of the breathing assistance apparatus when the barrier is not in the covering position.

In some configurations, the housing comprises an upper chassis and a lower chassis, wherein the upper chassis comprises the outer surface having a first colour, and wherein the lower chassis comprises the portion having a second colour.

Features from one or more embodiments or configurations may be combined with features of one or more other embodiments or configurations. Additionally, more than one embodiment may be used together during a process of respiratory support of a patient.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

1. Introduction

Figure 1:
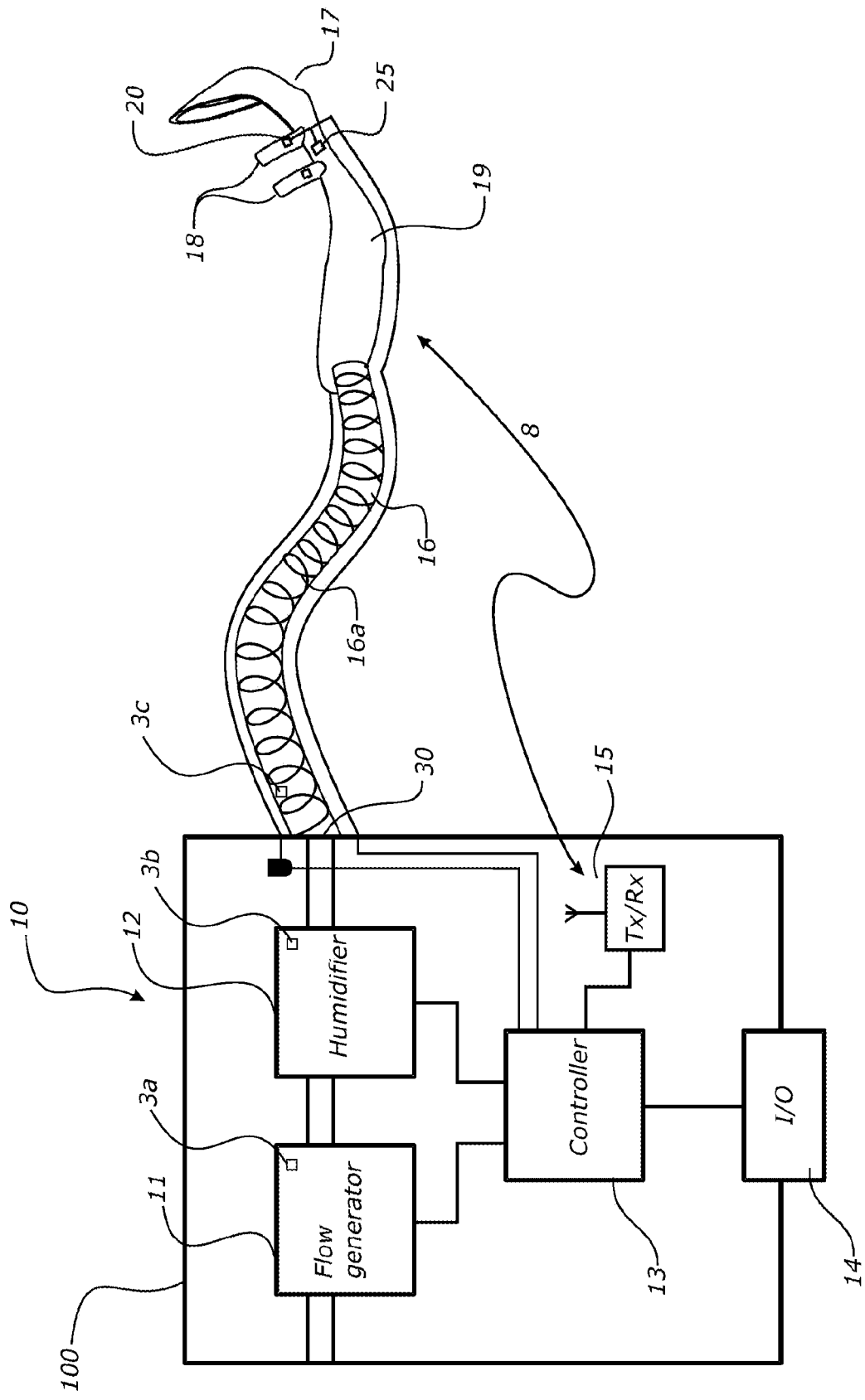
FIG. 1 shows in diagrammatic form a breathing assistance apparatus.

A breathing assistance apparatus 10 for delivering a flow of gas (which may contain one or more gases) to a patient is shown in FIG. 1. The apparatus 10 could, for example, be a CPAP apparatus or a high flow apparatus. An exemplary CPAP apparatus is described in WO 2011/056080. The contents of that specification are incorporated herein in their entirety by way of reference.

A CPAP apparatus is a gases supply and optionally gases humidification apparatus. The apparatus is operable to provide respiratory assistance to patients or users who require a supply of gas (humidified or otherwise) at positive pressure for the treatment of diseases such as Obstructive Sleep Apnea (OSA), snoring, or Chronic Obstructive Pulmonary Disease (COPD) and the like. A CPAP apparatus would typically include a humidifier liquid chamber, so as to form a combined assisted breathing unit and humidifier.

CPAP apparatuses, when used with a humidifier, typically have a structure where gases at a required pressure are delivered from an assisted breathing unit or blower unit to a liquid chamber downstream from the blower. As the gases pass through the liquid chamber, they become saturated with liquid vapour (e.g. water vapour). A flexible tubular gases conduit delivers the gases to a user or patient downstream from the humidifier chamber.

A high flow apparatus may be used to deliver a high gas flow or high flow therapy to a patient to assist with breathing and/or treat breathing disorders including chronic obstructive pulmonary disease (COPD). A high flow apparatus includes a gases supply and typically includes a humidification apparatus.

The breathing assistance apparatuses typically have one or more accessories such as a breathing conduit and a patient interface such as a cannula or mask for delivering gases to a patient. The conduit enables gases to be delivered from the housing of the breathing assistance apparatus to the patient. For example, the apparatus may be placed on a floor or other support surface, and the patient may be in a bed. The breathing assistance apparatus may have a recess for receipt of a humidifier liquid chamber. The liquid chamber will receive liquid from, for example, a flexible liquid bag that delivers liquid to a humidifier liquid chamber via one more tubes. Alternatively, the liquid chamber can be removed and refilled as required. The recess will contain a heater plate to heat the liquid chamber, to humidify gases passing through the liquid chamber. The humidified gases are then delivered to the patient.

In general terms, the apparatus 10 comprises a main housing 100 that contains a flow generator 11 in the form of a motor/impeller arrangement, a humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gas flow) for delivery to a patient, operating the humidifier 12 to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gas flow output or patient outlet port 30 in the housing 100 of the breathing assistance apparatus 10, and is coupled to a patient interface 17 such as a nasal cannula with a manifold 19 and nasal prongs 18. Additionally, or alternatively, the patient breathing conduit 16 could be coupled to a face mask. Additionally, or alternatively, the patient breathing conduit could be coupled to a nasal pillows mask, and/or a nasal mask, and/or a tracheostomy interface, or any other suitable type of patient interface. The gas flow, which may be humidified, that is generated by the breathing assistance apparatus 10 is delivered to the patient via the patient breathing conduit 16 through the patient interface 17. The patient breathing conduit 16 can have a heater wire 16a to heat gas flow passing through to the patient. The heater wire 16a is under the control of the controller 13. The patient breathing conduit 16 and/or patient interface 17 can be considered part of the breathing assistance apparatus 10, or alternatively peripheral to it. The breathing assistance apparatus 10, breathing conduit 16, and patient interface 17 may together form a breathing assistance system or, in some configurations, a flow therapy system.

General operation of an exemplary breathing assistance apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and/or controls the humidifier 12 to humidify the gas flow and/or heat the gas flow to an appropriate level. The gas flow is directed out through the patient breathing conduit 16 and patient interface 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with, or can determine, a suitable target temperature of the gas flow.

Operation sensors 3a, 3b, 3c, 20, and 25, such as flow, temperature, humidity, and/or pressure sensors, can be placed in various locations in the breathing assistance apparatus 10 and/or the patient breathing conduit 16 and/or patient interface 17. Output from the sensors can be received by the controller 13, to assist it to operate the breathing assistance apparatus 10 in a manner that provides optimal therapy. In some configurations, providing optimal therapy includes meeting a patient's inspiratory flow. The apparatus 10 may have a transmitter and/or receiver 15 to enable the controller 13 to receive signals 8 from the sensors and/or to control the various components of the breathing assistance apparatus 10, including but not limited to the flow generator 11, humidifier 12, and heater wire 16a, or accessories or peripherals associated with the breathing assistance apparatus 10. Additionally, or alternatively, the transmitter and/or receiver 15 may deliver data to a remote server or enable remote control of the apparatus 10.

The breathing assistance apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute (LPM) to about seventy liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

For example, in some configurations, for an adult patient 'high flow therapy' may refer to the delivery of gases to a patient at a flow rate of greater than or equal to about 10 liters per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may, in some configurations, deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory flow, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available for each and every breath, while minimising re-breathing of carbon dioxide, nitrogen, etc.

In one example for high flow therapy, an unsealed or non-sealing user interface, e.g. a nasal cannula, is used. For CPAP a sealed interface is typically used, e.g. a nasal mask, full face mask, or nasal pillows.

The patient interface 17 may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As described below, the breathing assistance apparatus 10 has various features to assist with the functioning, use, and/or configuration of the breathing assistance apparatus 10.

As shown in FIGS. 2 to 6, a first configuration breathing assistance apparatus 10 comprises a breathing assistance apparatus base unit 50 having a main housing 100. The main housing 100 has a main housing upper chassis 102 and a main housing lower chassis 104.

The main housing of the base unit 50 has a peripheral wall arrangement. The peripheral wall arrangement defines a recess 108 that provides a humidifier liquid chamber bay for receipt of a removable liquid chamber 151. The removable liquid chamber 151 contains a suitable liquid such as water for humidifying gases that will be delivered to a patient.

The base unit 50 of the apparatus 10 has a guard 200 that will be described in more detail below. A barrier 251 of the guard overlaps part of the liquid chamber 151 when the barrier of the guard is in a covering position and the liquid chamber is in the recess 108, and exposes the part of the liquid chamber 151 when the barrier of the guard 200 is in an access position and the liquid chamber 151 is in the recess.

In the form shown, the main housing lower chassis 104 peripheral wall arrangement comprises a substantially vertical left side outer wall 109 that is oriented in a front-to-rear direction of the main housing 100, a substantially vertical right side outer wall 111, and a substantially vertical rear outer wall 113 that extends between and connects the walls 109, 111. A bottom wall 115 extends between and connects the lower ends of walls 109, 111, 113, and forms a base of the apparatus and a substantially horizontal floor portion of the liquid chamber bay.

The floor portion of the recess 108 has a receptacle portion 108a to receive a heater arrangement such as a heater plate 140 or other suitable heating element(s) for heating liquid in the liquid chamber 151 for use during a humidification process. The heater plate 140 would typically have a shape that substantially corresponds to the shape of a base 154 of the liquid chamber 151, such as a circular shape for example. The heater plate 140 is resiliently mounted; for example, on biasing device(s) such as spring(s). The resilient mounting enables the heater plate to move downwardly to accommodate the liquid chamber 151 in the recess 108, while maintaining good contact between the heater plate 140 and the base of the liquid chamber once the liquid chamber is inserted in the recess 108.

The main housing lower chassis 104 is attachable to the upper chassis 102, either by suitable fasteners or integrated attachment features such as clips for example. When the main housing lower chassis 104 is attached to the main housing upper chassis 102, the walls of the upper and lower chassis engage with each other.

Figure 6:
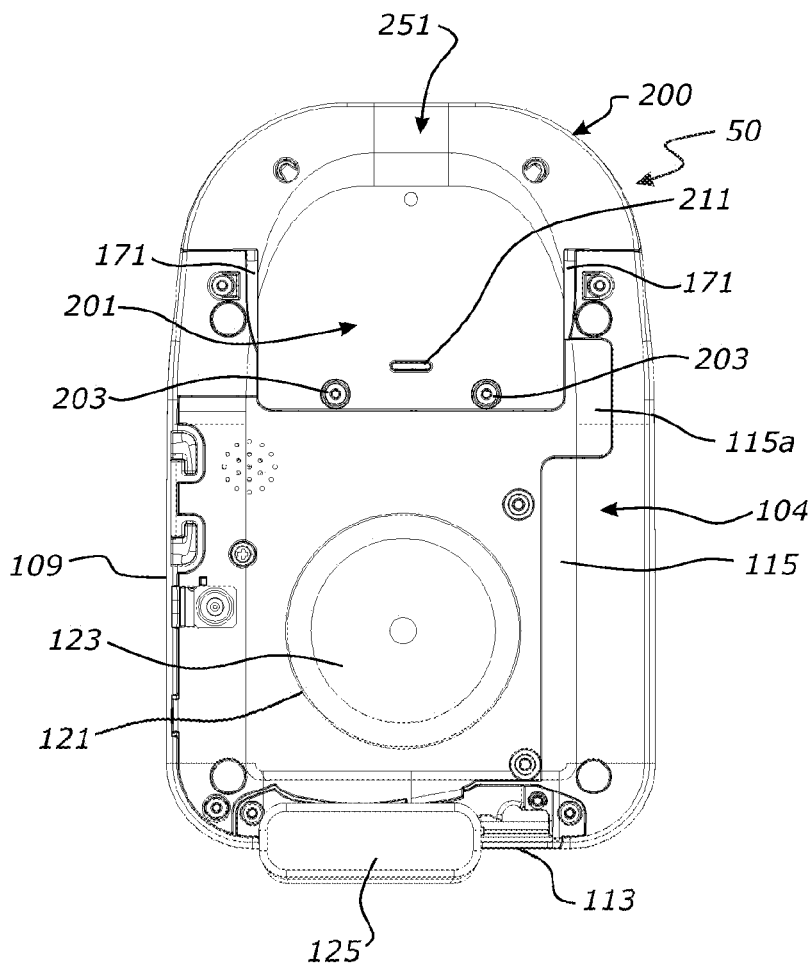
FIG. 6 is a bottom view of the breathing assistance apparatus base unit.

As shown in FIG. 6, the lower chassis 104 has a motor recess 121 for receipt of a motor module which may be permanently inserted in the recess or may be removable from the recess. A recess opening is provided in the bottom wall 115 adjacent a rear edge thereof, for receipt of the removable motor module. A base 123 of the motor module covers the opening into the motor recess 121. The motor module comprises a motor that forms a blower to cause gas flow, and may comprise one or more sensors to sense properties of the gas passing through the motor module. The motor module may comprise sensor(s) to sense parameters of gases flowing through the motor module.

The motor module and housing of the base unit 50 of the apparatus 10 are provided with suitable tubes and/or gas flow passages to deliver gases from one or more gases inlets of the base unit 50 of the apparatus, to a gas inlet port 157 of the liquid chamber 151 to humidify the gases. The gases are delivered from a gas outlet port 159 of the liquid chamber 151 to the patient outlet port 30 and thereby to the patient via the patient breathing conduit 16 and patient interface 17.

In the form shown, the motor recess 121 comprises a recess opening in a bottom wall of the housing 100. Alternatively, the recess opening could be in a different part of the housing 100, such as a side, front, or top of the housing 100.

The base unit 50 of the apparatus 10 may have a battery 125 to provide power to the apparatus when there is a power outage or for portable use. The battery may be replaceable.

In the form shown, the battery 125 is coupled to an exterior of the back wall of the apparatus housing 100. This provides a large surface area to cool the battery and reduces the amount of heat entering the apparatus from the battery. Additionally, this configuration reduces the influence of heat generated by components of the apparatus on the battery, particularly when the battery is being charged. In an alternative configuration, the battery may be internally mounted in the main housing.

Figure 4:
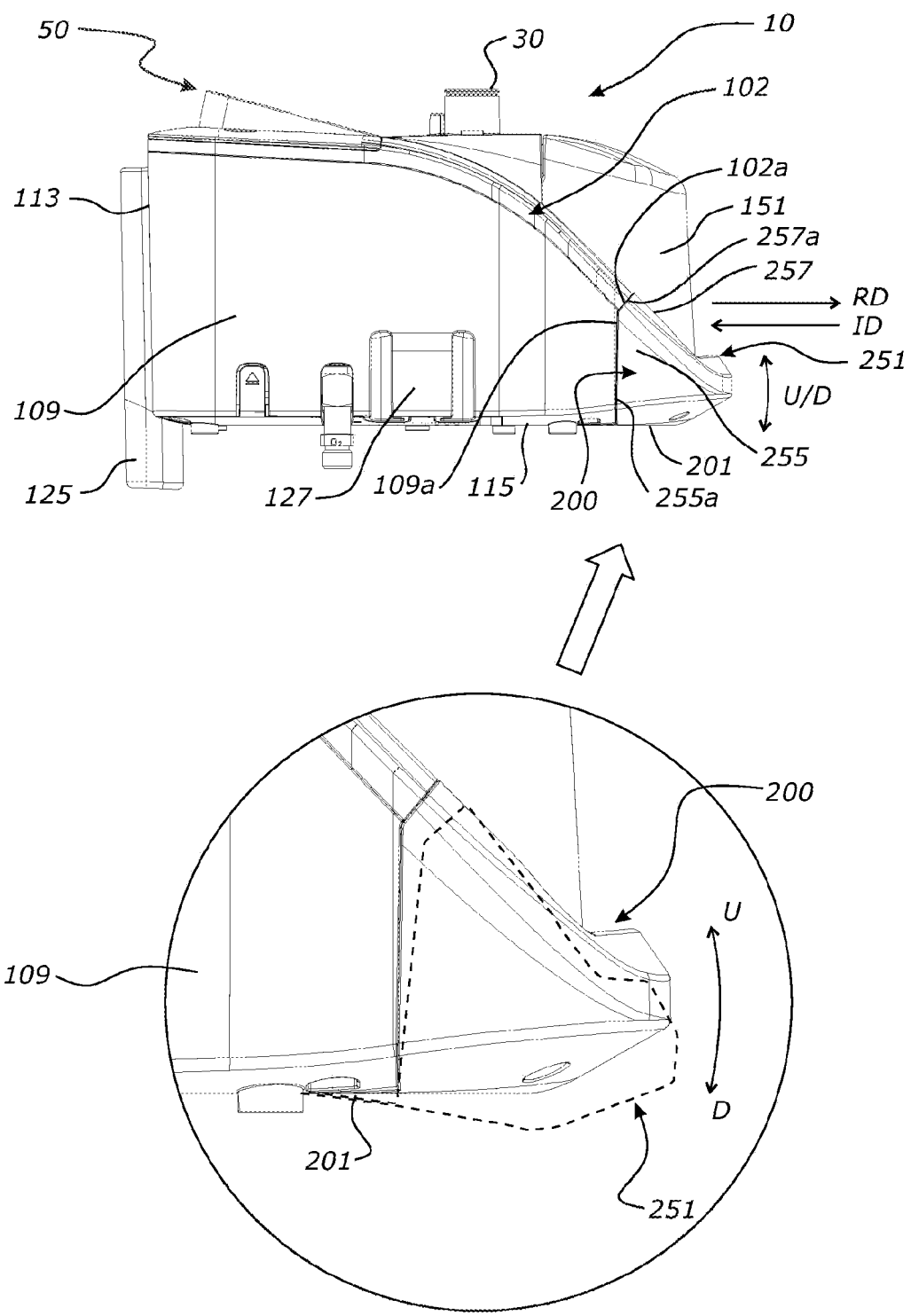
FIG. 4 is a left side view of the breathing assistance apparatus base unit with the liquid chamber positioned in the recess.
Figure 5:
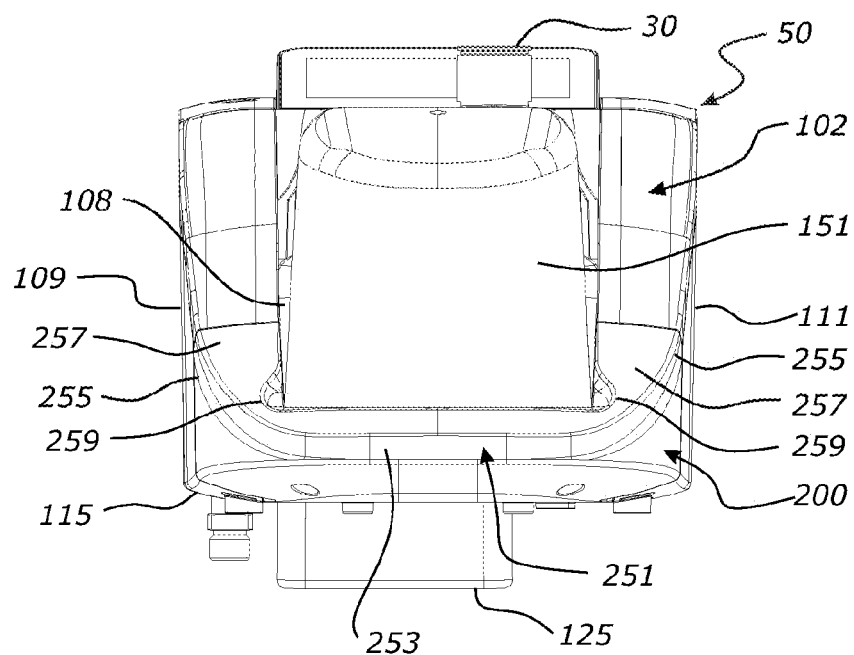
FIG. 5 is a front view of the breathing assistance apparatus base unit with the liquid chamber positioned in the recess.

As shown in FIG. 4, the base unit 50 of the apparatus 10 has a mounting feature 127 for mounting the apparatus to a support apparatus.

The mounting feature 127 may be integrally formed with part of the main housing 100 of the base unit 50 of the apparatus 10. In the form shown, the mounting feature 127 is integrally formed with the left side wall 109 the lower chassis 104 of the housing 100. The mounting feature 127 could instead be integrally formed with any of the other walls of the housing 100, such as a rear wall, right side wall, or other wall.

The main housing 100 of the apparatus may be formed from any suitable material that will allow the mounting feature 127 to be integrally formed. For example, the housing 100 may be formed from polycarbonate.

The integral mounting feature 127 has greater impact strength compared to an additional, screwed in part. Strengthening of the mounting feature 127 may also be done by, for example, varying the wall thickness, ribbing, or varying in internal geometries.

Figure 3:
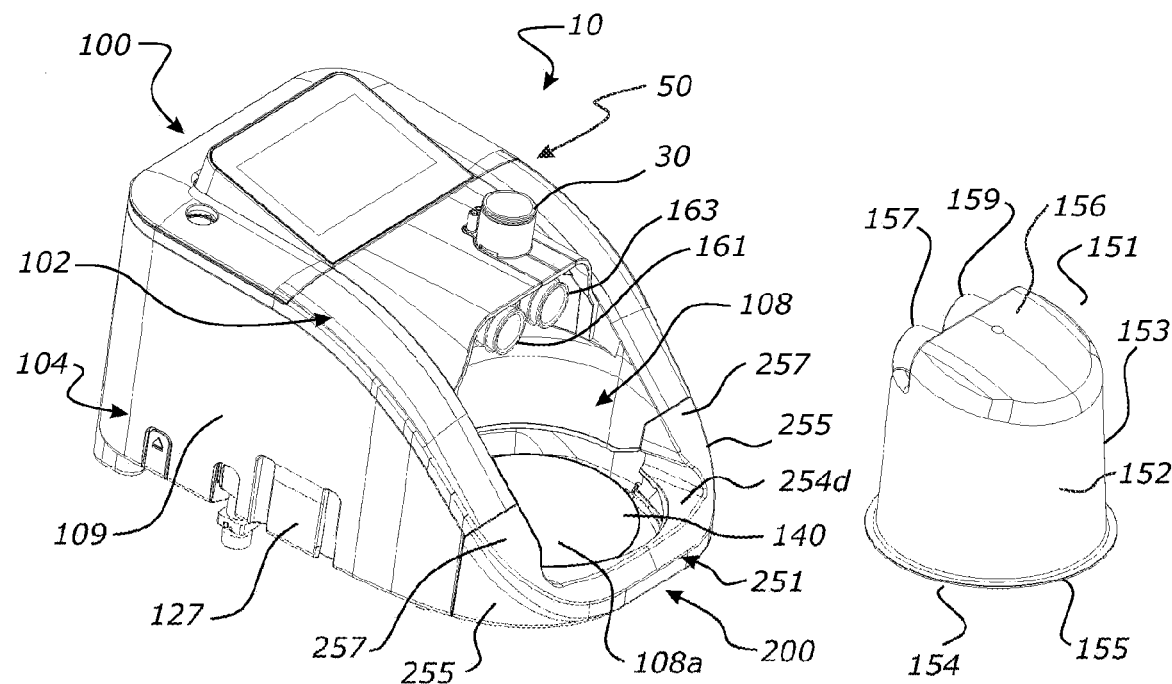
FIG. 3 is a front/left side overhead perspective view of the breathing assistance apparatus with the liquid chamber removed from the recess of the breathing assistance apparatus base unit.

FIG. 3 shows a humidifier liquid chamber 151 for use with the breathing assistance apparatus 10. The chamber 151 is a removable liquid chamber to be filled with liquid such as water for the humidification of respiratory gases. The liquid chamber 151 is removable from the base unit 50 of the breathing assistance apparatus 10 to be more easily re-filled or disposed of.

The liquid chamber 151 has a body 152 having a peripheral wall 153 and a roof 156. The body defines an internal chamber for receipt of a liquid. A base 154 of the liquid chamber is provided at a lower end of the peripheral wall, and a base flange 155 of the base 154 projects outwardly from the lower end of the peripheral wall 153. The base 154, including the base flange 155, will typically be a highly heat conductive material. First and second base unit connection ports comprising a liquid chamber gas inlet port 157 and a liquid chamber gas outlet port 159 are in communication with the internal chamber of the liquid chamber 151. The breathing assistance apparatus base unit 50 comprises complementary chamber connection ports comprising a gas outlet port 161 and a humidified gas inlet port 163. When the liquid chamber is received in the recess 108 to engage with the housing 100, the liquid chamber gas inlet port 157 couples to the gas outlet port 161 (FIG. 14) that receives gases from the motor module, and the liquid chamber gas outlet port 157 couples to the humidified gas inlet port 163 (FIG. 3) to deliver humidified gases from the liquid chamber to the patient outlet port 30.

The liquid chamber 151, and the base flange 155 of the liquid chamber, could have a substantially circular peripheral shape, or could be any other suitable shape, with the recess 108 shape modified accordingly if required.

In the form shown, the liquid chamber 151 has a has a substantially cylindrical shape.

The base 154 of the liquid chamber is heat conductive. In particular, the base 154 of the liquid chamber 151 is made from a highly heat conductive material, which allows heating of the liquid in the chamber when in contact with the heater plate 140 of the base unit 50 of the breathing assistance apparatus 10 during use.

The liquid chamber 151 can be fluidly coupled to the base unit 50 of apparatus 10 in a slide-on motion in a rearward insertion direction ID of the liquid chamber 151 into the recess 108, from a position at the front of the housing 100 in a direction toward the rear of the housing 100. That is, the recess 108 is configured to removably receive the liquid chamber 151 by moving the liquid chamber in the rearward insertion direction into the recess 108, with the back of the base flange 155 inserted first.

The gas outlet port 161 is in fluid communication, via a fixed L shaped elbow, with a gas flow passage from the motor/impeller unit. The liquid chamber 151 may initially be inserted into the recess 108 on an angle, then rotated to horizontal, with an end part of the motion as the ports 157, 159 of the liquid chamber engage with the ports 161, 163 of the apparatus 10 being a linear motion. The humidified gas inlet port 163 is embodied in a removable elbow.

The removable elbow is L-shaped, and further comprises the patient outlet port 30 for coupling to the patient breathing conduit 16 to deliver gases to the patient interface 17. The gases outlet port 161, humidified gas inlet port 163, and patient outlet port 30 each comprise soft seals such as wiper seals, L-seals, X-rings, or O-rings to provide a sealed gases passageway between the apparatus 10, the liquid chamber 151, and the patient breathing conduit 16 and optionally one or more other accessories.

The gas outlet port 161 and gas inlet port 163 comprise multiple sealing elements. The sealing elements may be wiper seals, L-seals, X-rings, or O-rings. The wiper seals may have a T-shaped cross-section. The gas outlet port 161 and the gas inlet port 163 may each comprise two, three, or more sealing elements. In one configuration, each of the gas inlet port 163 and gas outlet port 161 comprises a pair of wiper seals. In this configuration, the gas inlet port 163 has two wiper seals positioned adjacent each other on the gas inlet port 163. Similarly, the gas outlet port 161 comprises a pair of wiper seals positioned adjacent each other on the gas outlet port 161. The pair of wiper seals (or of the other types of sealing elements) on each port 161, 163 improves the seal with the corresponding base unit connection ports 157, 159 and provides improved protection against liquid ingress into the interior of the housing of the base unit 50 of the apparatus where electronics are located. When the liquid chamber 151 is coupled to the gas inlet port 163 and gas outlet port 161 of the base unit 50, one wiper seal may be positioned inside each base unit connection port 157, 159 and one wiper seal may be located outside each base unit connection port 157, 159, when the liquid chamber is assembled with the base unit 50. Alternatively, both wiper seals are positioned inside the respective base unit connection ports 157, 159 when the liquid chamber 151 is assembled onto the heater plate 140 in the recess 108. The arrangement of using two wiper seals per port 161, 163 provides redundancy for liquid ingress. Similar arrangement can be used for L-seals, X-rings, or O-rings. The gas outlet port 161 and gas inlet port 163 of the base unit 50 are structured to have an elongate portion; i.e., a length of the ports 161, 163 is such that the wiper seals, L-seals, X-rings, or O-rings are retained on the ports 161, 163.

The gas inlet port 157 of the liquid chamber is complementary with the gas outlet port 161 of the breathing assistance apparatus base unit 50, and the gas outlet port 159 of the liquid chamber is complementary with the humidified gas inlet port 163 of the breathing assistance apparatus base unit 50. The axes of those ports are preferably parallel and/or horizontal to enable the liquid chamber 151 to be inserted into the chamber bay 108 in a substantially linear movement to form gas connections between the ports.

The chamber connection ports 161, 163 are parallel cylindrical features extending from the housing of the breathing assistance apparatus base unit 50. The ports 161, 163 will typically have an equal profile, and equal length, and axes located on the same horizontal plane. The ports 161, 163 will typically terminate on the same vertical plane at their distal ends. The ports 161, 163 have a port separation distance or pitch, which is the horizontal distance between the centre or axis of each port 161, 163. This is substantially equal to the horizontal distance between the centres of the base unit connection ports 157, 159 of the liquid chamber.

The chamber connection ports 161, 163 (which in the form shown are male connection members) of the breathing assistance apparatus base unit 50 insert into the base unit connection ports 157, 159 (which in the form shown are female connection members) of the liquid chamber in a concentric manner. The inner diameter of the base unit connection ports 157, 159 is larger than the outer diameter of the chamber connection ports 161, 163.

The liquid chamber 151 may initially be inserted into the recess 108 on an angle, and then tilted to be substantially horizontal, so that a rear part of movement of the liquid chamber 151 is substantially linear. The recess 108 may comprise one or more guide rails to assist with holding the liquid chamber in position in the recess 108.

The breathing assistance apparatus 10 may have any one or more of the features and/or functionality of the breathing assistance apparatus described and shown in WO2016/207838A9 (W0'838). The contents of that specification are incorporated herein in their entirety by way of reference.

The base unit 50 of the breathing assistance apparatus comprises a guard 200 mounted to the housing 100. The guard is configured to minimise the likelihood of a user touching the base 154 of the liquid chamber 151, and more particularly the base flange 155 of the base 154 of the liquid chamber 151. In some configurations, the guard 200 may be configured to minimise the likelihood of a user touching the heater plate 140 in the base of the recess 108 and/or to assist with maintaining the liquid chamber 151 in engagement with the breathing assistance apparatus 10. The guard is shown mounted to the housing in FIGS. 2 to 6, and separately from the housing in FIGS. 7 to 10.

The guard 200 comprises a base 201 and a barrier 251. The barrier 251 is movable relative to the housing between a raised covering position (shown in solid lines in FIG. 4 for example) in which the barrier 251 partly covers the recess 108 and overlaps the front edge of the base flange 155 of the liquid chamber, and a lowered access position (shown in broken lines in the inset to FIG. 4) in which the recess 108 is less covered or is uncovered by the barrier 251 and the barrier 251 exposes the front edge of the base flange 155 of the liquid chamber. The base 201 of the guard flexes during that movement. The guard 200 can be moved by a user actuating the guard 200. The guard 200 is configured to be actuated by pressing on the barrier 251, downwardly in the configuration shown in the figures. The base 201 of the guard extends under the base of the housing 100. The base 201 of the guard 200 is mounted to a base of the housing 100, and more particularly is mounted to an exterior of the bottom wall 115 of the housing 100. The base 201 of the guard 200 is substantially flat when it is in its unflexed rest state.

Figure 13:
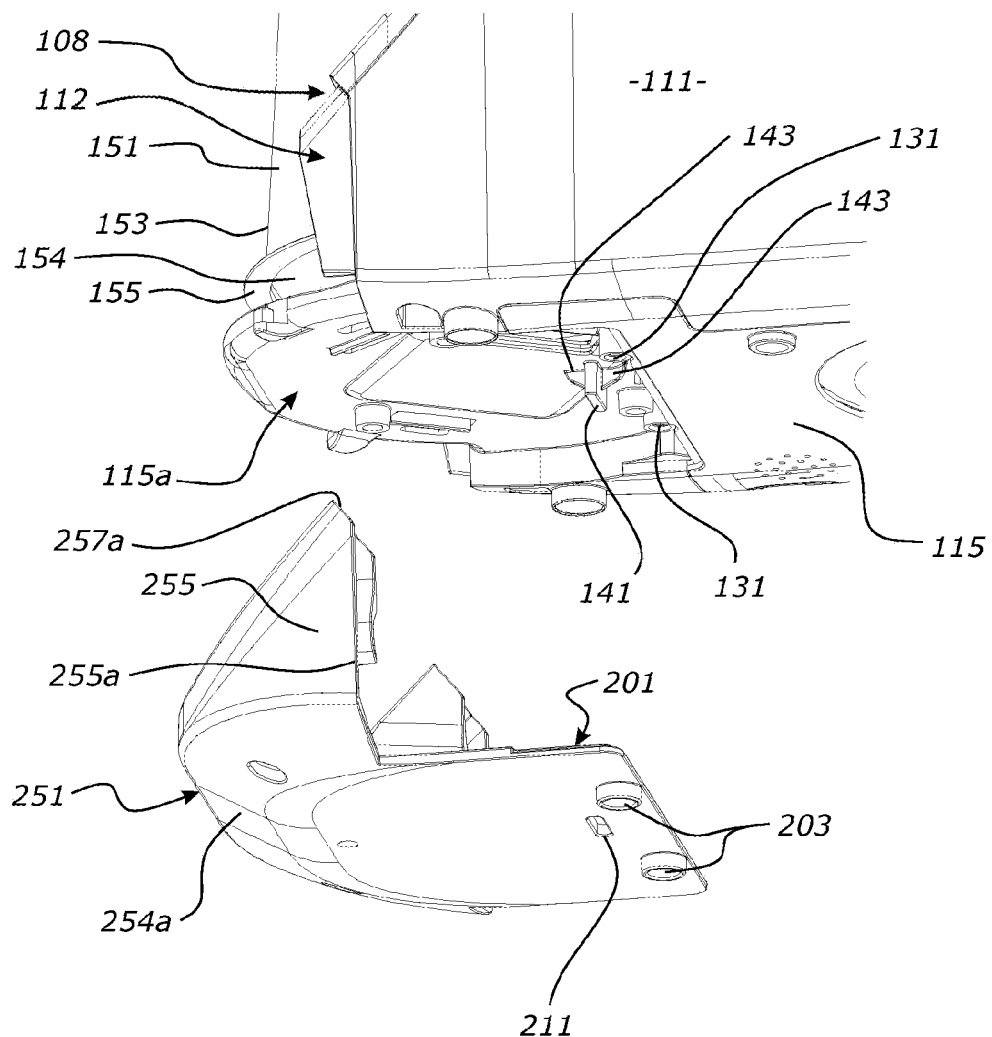
FIG. 13 is an exploded right-side underside perspective view of the guard and part of the housing of the breathing assistance apparatus base unit.

In the form shown, the base 201 of the guard 200 is mounted to the base of the housing 100 by one or more fasteners 205. In the form shown in FIG. 9 for example, the base 201 of the guard 200 comprises one or more fastener-receiving apertures 203 positioned at or adjacent a first end 201a of the base 201. The first end 201a of the base is configured to mount to the housing 100 at a position spaced from a forward end of the housing 100. As shown in FIG. 13, a mounting recess 115a is provided at the front of the bottom wall 115 of the housing 100. The mounting recess 115a is configured to receive the base 201 of the guard 200. The mounting recess 115a is provided beneath the recess 108 for receipt of the liquid chamber 151.

In the form shown, the base 201 of the guard 200 has two fastener-receiving apertures 203. In alternative configurations, the base 201 of the guard could have one, three, four, or more fastener receiving apertures 203.

Figure 11:
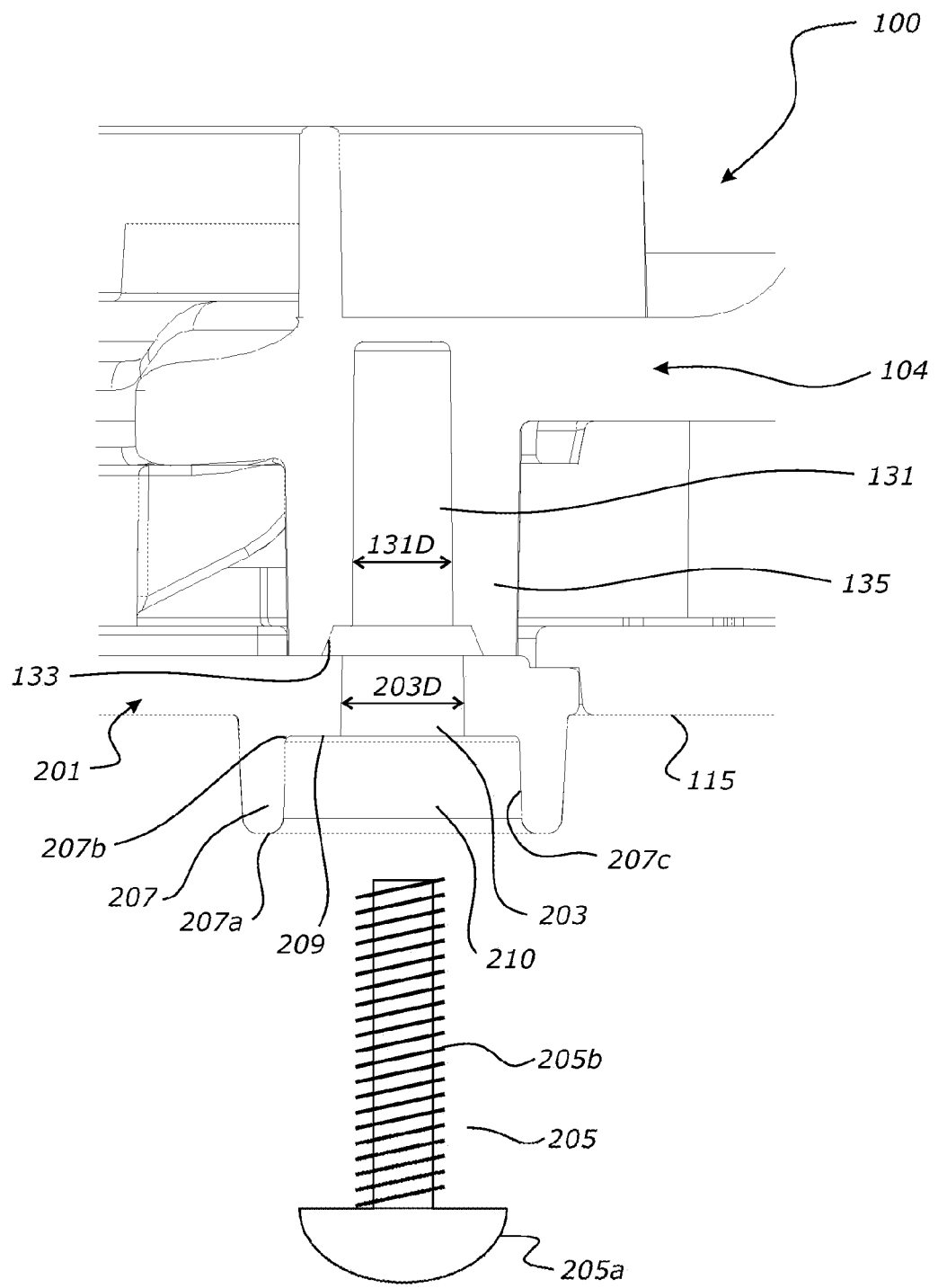
FIG. 11 is a sectional view through one of the mounting arrangements for mounting the guard to the housing of the breathing assistance apparatus base unit.

FIG. 11 shows a side sectional view through the mounting region of the guard 200 to the housing 100. The guard comprises a cylindrical extension 207 that extends downwardly from the underside of the base 201. The cylindrical extension 207 has a free end 207a and a connected end 207b. A substantially flat ceiling portion 209 is provided in the interior of the cylindrical extension 207. The inner wall 207c of the cylindrical extension and the ceiling portion 209 define a recess 210 for receipt of the head 205a of the fastener 205. The fastener-receiving aperture 203 has a smaller diameter than the recess 210, and extends upwardly from the recess 210. When the faster is coupled to the apparatus, the shank 205b of the fastener will extend through the fastener-receiving aperture 203 into the housing 100, and the head 205a of the fastener will be positioned in the recess 210 and will abut against the ceiling 209. The fastener 205 could be any suitable type, such as a screw, push-pin, or another type for example.

When the guard 200 is assembled to the housing 100, each fastener-receiving aperture 203 is aligned with a respective fastener-receiving recess 131. The fastener-receiving recess 131 has a tapered lead-in feature 133 that allows the fastener shank 205b to be inserted through the fastener-receiving aperture 203 and into the fastener-receiving recess 131, even if the components are not perfectly aligned. The fastener 205 will push the components into alignment when the fastener is further inserted.

The fastener-receiving recess 131 is provided in a cylindrical protrusion 135 that projects downwardly from the housing 100. With that configuration, the cylindrical protrusions 135 may be the only portion of the housing 100 that contacts the upper surface of the base 201 of the guard 200. That enables the base 201 of the guard to flex uninhibited by further contact between the guard 200 and the housing 100. In an alternative configuration, the fastener-receiving recess 131 may extend upwardly into a wall of the housing 100 without a cylindrical protrusion.

In the configuration shown in FIG. 11, the diameter 203D of the fastener-receiving aperture 203 in the base 201 of the guard, is slightly larger than the diameter 131D of the fastener-receiving recess 131 in the housing 100. That allows the fastener 205 to engage in the fastener-receiving recess 131 in the housing 100 without contacting the inner wall 207c of the cylindrical extension. Therefore, the fastener 205 only applies a force that holds the guard 200 and the housing 100 together, without applying any substantial lateral force or loading.

The guard 200 and/or housing 100 may comprise one or more other features to minimise the application of lateral loading to the fasteners 205 that mount the guard 200 to the housing 100, as the guard 200 is actuated by a user.

Figure 12:
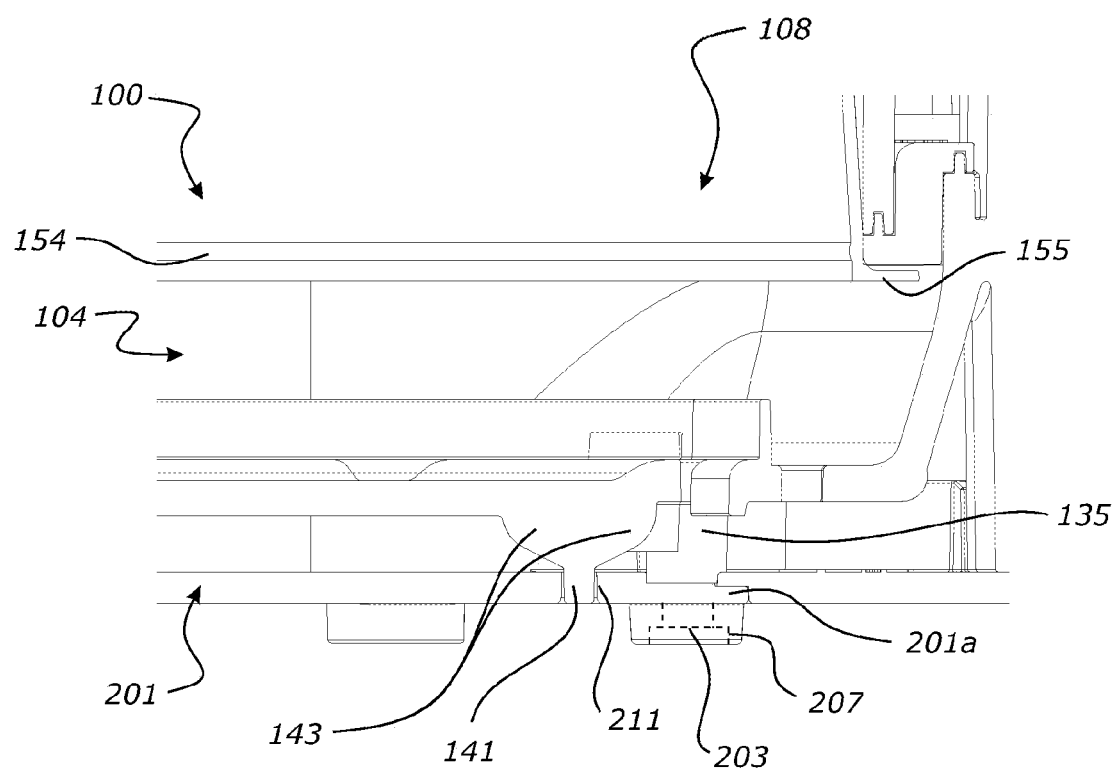
FIG. 12 is a sectional view through an alignment protrusion of the housing extending through a complementary aperture in the guard.

Referring to FIGS. 12 and 13, the housing 100 comprises a downwardly-extending alignment projection 141 and the base 201 of the guard 200 comprises a complementary alignment aperture 211 to receive the projection 141 to resist horizontal movement of the base 201 of the guard during flexing of the guard. This is suitable when a fastener 205 is used that is unsuited to resisting lateral forces, such as a screw for example. The alignment projection 141 extends downwardly from a wall of the housing 100. The alignment projection 141 and the alignment aperture 211 are positioned close to the first end 201a of the base 201 and close to the fastener-receiving apertures 203. The alignment projection 141 and the alignment aperture 211 are configured such that they allow for vertical flexing in the base 201 of the guard 200 while inhibiting horizontal movement.

As discussed below, in some configurations the guard 200 can be actuated by inserting and/or removing the liquid chamber 151 to/from the recess 108. When the liquid chamber 151 is inserted and removed, the contact between the liquid chamber 151 and the barrier 251 may apply force to the guard in a horizontal direction. In this situation the horizontal movement is prevented by the alignment protrusion 141 contacting the peripheral wall of the alignment aperture 211.

As shown in FIG. 12, the alignment aperture 211 can be slightly larger than the alignment protrusion 141 to accommodate slight horizontal translation when the base 201 of the guard 200 flexes vertically. The spacing between the alignment protrusion 141 and the alignment aperture 211 will allow liquid to drain from the upper surface of the base 201, if there is any leakage of liquid from the liquid chamber 151 during insertion or removal of the liquid chamber into/from the recess 108.

As shown in FIGS. 12 and 13, the alignment protrusion 141 may have one or more support members 143 to provide stability to the alignment protrusion during loading. In the form shown, forward and rearward arcuate segment support members 143 are positioned adjacent the alignment protrusion 141. Alternatively, a different number or shape of the support members 143 may be provided, or no support members 143 may be provided.

The housing 100 may have one, two, or more alignment protrusions 141, and the base 201 of the guard 200 may have a corresponding number of alignment apertures 211. If an alternative type of fastening that can accommodate lateral loading is used to mount the guard 200 to the housing 100 (such as integrated fastening features), the alignment protrusion(s) 141 and alignment aperture(s) may not be provided.

The guard 200 is fastened to the exterior of the housing so that the guard 200 is replaceable without disassembling the housing 100 of the base unit 50 of the breathing assistance apparatus 10. The guard 200 can be removed from the housing 100 by removing the fastener(s). This is useful if the barrier is configured to act as a bumper.

In one configuration, the guard 200 covers a front exterior part of the recess 108. Alternatively, the recess could be open to a different part of the housing 100, such as a side exterior of the housing 100 or a rear exterior of the housing, and the guard 200 could accordingly cover the side exterior part of the recess or the rear exterior part of the recess.

The guard 200 may have a colour that is representative of the intended function of the breathing assistance apparatus 10. The colour could indicate whether the breathing assistance apparatus is for use in the home or in the hospital. The colour could indicate what therapy the breathing assistance apparatus provides, such as non-invasive ventilation (NIV), CPAP, bubble CPAP, resuscitation, or nasal high flow. The colour could indicate the model of the breathing assistance apparatus.

The guard 200 can easily be removed and replaced by a guard 200 of a different colour representing a different intended function of the breathing assistance apparatus 10. By fastening the guard 200 to the exterior of the housing 100, the different guards can easily be attached late in the manufacturing process once the configuration for the breathing assistance apparatus 10 has been decided. Additionally, if the breathing assistance apparatus 10 needed to be repurposed to serve a different function, it would be a simple process to remove the guard 200 and swap it out for a different coloured guard 200.

The barrier 251 of the guard extends from the base 201 of the guard at a location that is distal to the mounting of the base 201 to the housing 100. The barrier 251 of the guard extends upwardly from a position at or adjacent an opposite second forward end 201b of the base 201 so as to be located at the front of the base 201.

By fastening the guard 200 to the base of the base unit 50 of the breathing assistance apparatus 10, with the front of the guard covering and protruding from the front of the base unit 50 of the breathing assistance apparatus 10, the guard 200 acts as a front bumper for the breathing assistance apparatus 10. The guard 200 would protect the base unit 50 of the breathing assistance apparatus 10 during collisions, such as when a user drops the base unit 50 of the breathing assistance apparatus 10, or when the base unit 50 of the breathing assistance apparatus 10 collides with an object during movement (such as when the breathing assistance apparatus 10 is connected to a pole of a bed that is being transported). During such collisions, the guard 200 would be the only part of the breathing assistance apparatus 10 that would be damaged, and can easily be replaced by removing any fasteners 205, without having to further disassemble other parts of the breathing assistance apparatus 10.

Referring to FIGS. 5 and 7-10, the barrier 251 comprises a transversely extending body portion 253 and two upstanding portions 255 at or adjacent respective sides of the transversely extending body portion. Each upstanding portion 255 comprises an enlarged upper finger contact region 257 for a user to press on to actuate the guard 200.

Figure 7:
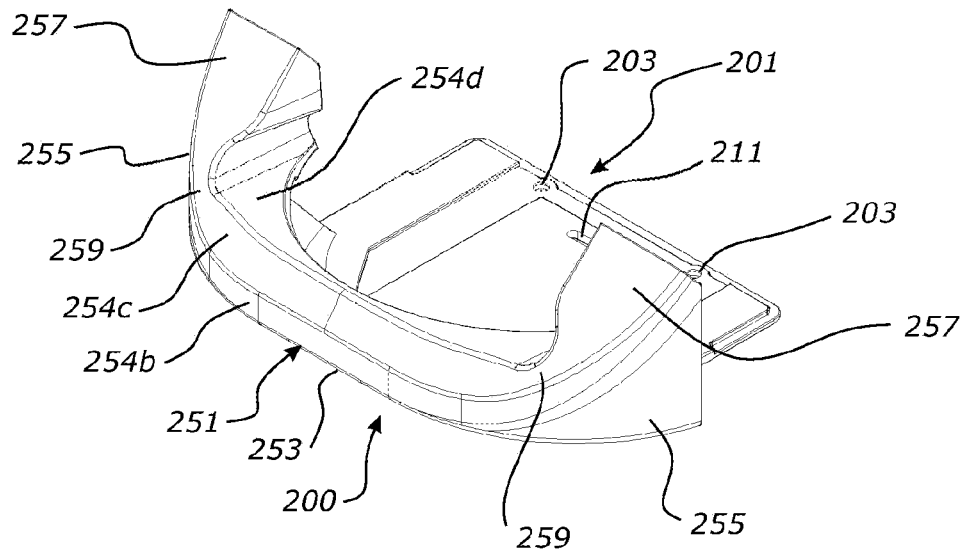
FIG. 7 is a front/right side overhead perspective view of a guard of the breathing assistance apparatus base unit.
Figure 8:
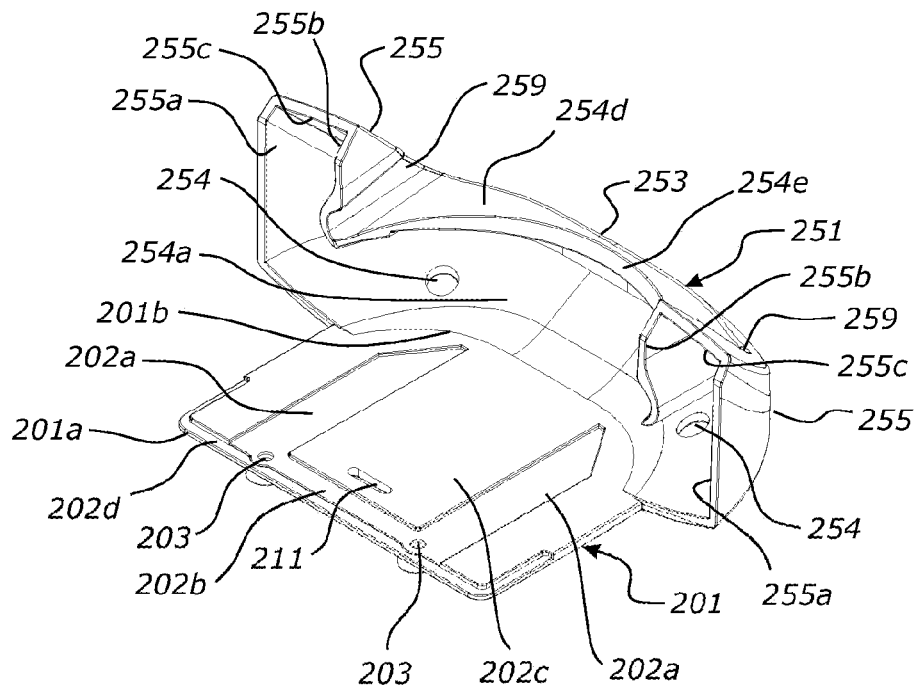
FIG. 8 is a rear/left side overhead perspective view of the guard.
Figure 9:
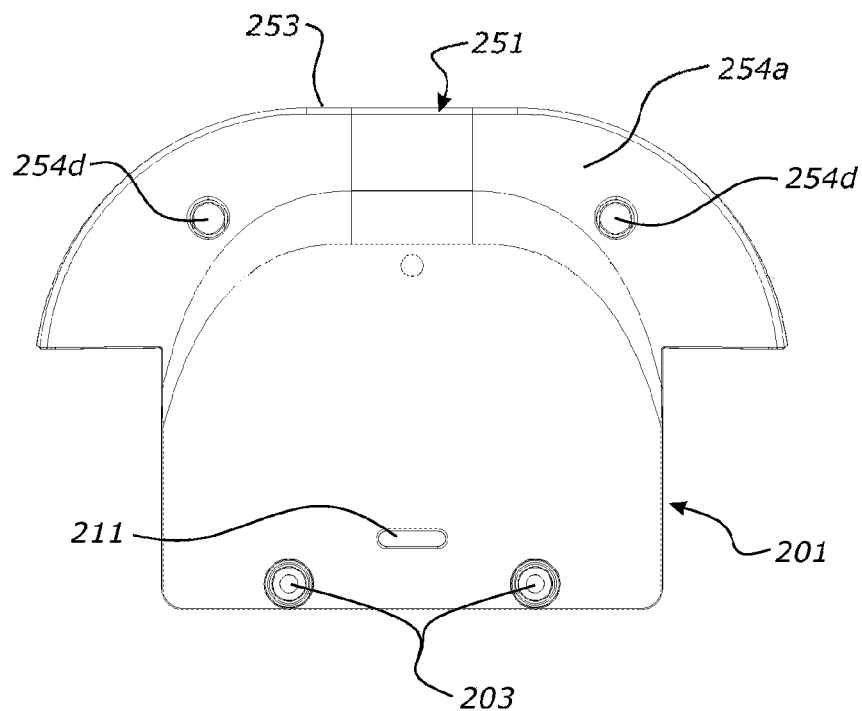
FIG. 9 is a bottom view of the guard.
Figure 16:
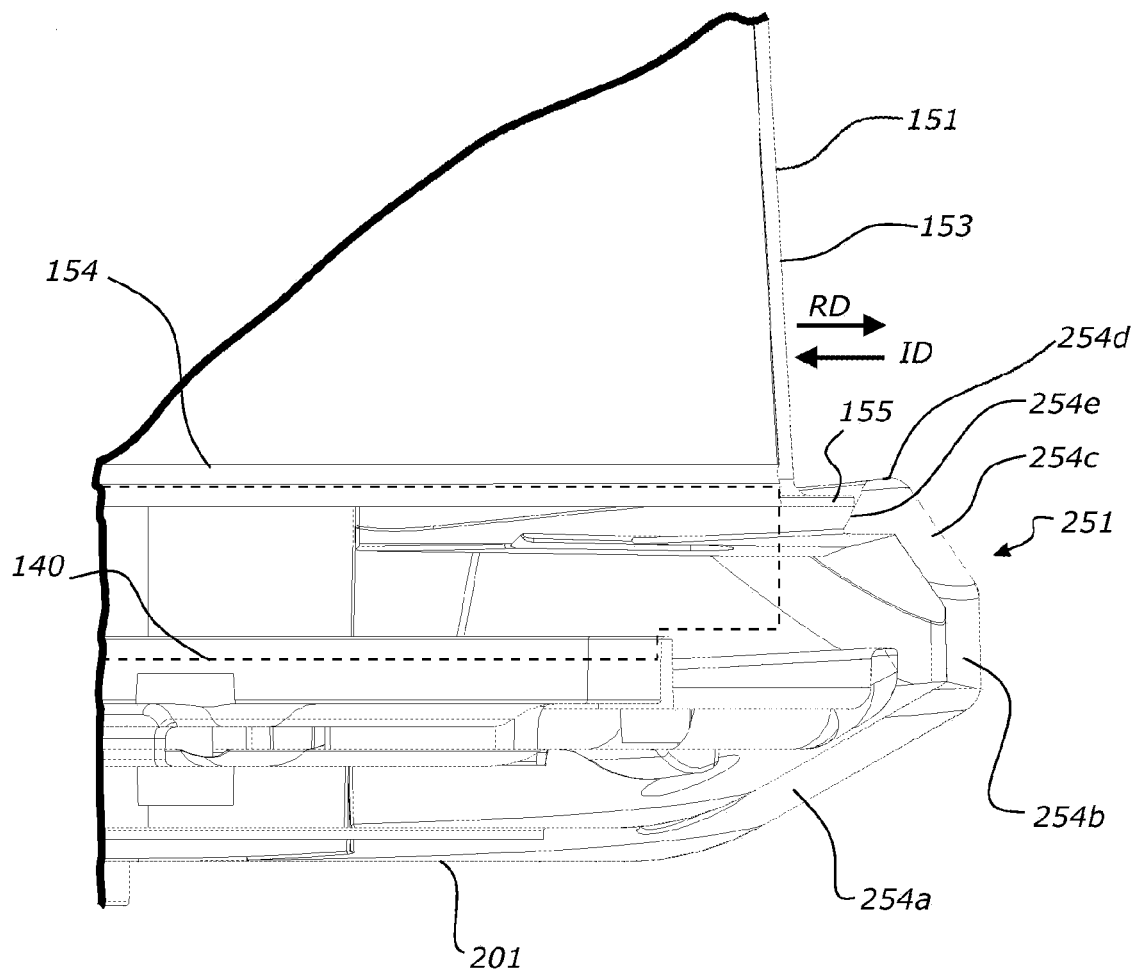
FIG. 16 is a part sectional left side view of the breathing assistance apparatus base unit, showing the position of the base of the liquid chamber relative to the barrier of the guard.

The shape of the barrier 251 is complementary to the shape of front end of the housing 100. As shown in FIGS. 7, 8, and 16, the barrier 251 comprises a lower wall portion 254a that extends upwardly and forward from the front end 201b of the base 201 and that is concave when viewed from above. An upstanding wall portion 254b extends upwardly from the lower wall portion and is convex when viewed from the front. An angled forward wall portion 254c extends upwardly and rearwardly from the top of the upstanding wall portion 254b. A rearwardly projecting upper wall portion 254d extends rearwardly and slightly downwardly from the upper end of the angled forward wall portion 254c and forms an upper edge of the transversely extending body portion 253. The rearwardly projecting upper wall portion 254d terminates at a downwardly and rearwardly angled rear wall portion 254e. The rearwardly projecting upper wall portion 254d and the downwardly and rearwardly angled rear wall portion 254e have an arcuate shape in plan view that corresponds substantially to the peripheral shape of the peripheral wall 153 of the liquid chamber 151.

Figure 2:
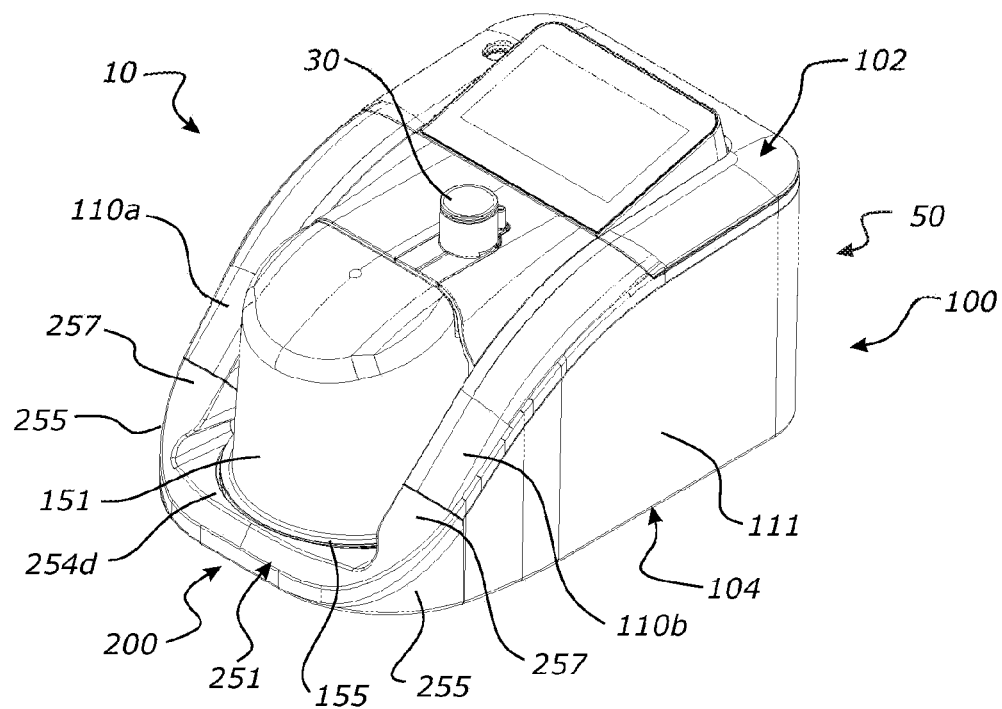
FIG. 2 is a front/right side overhead perspective view of a breathing assistance apparatus with a liquid chamber positioned in the recess of the breathing assistance apparatus base unit.

As shown in FIG. 4, the upper finger contact region 257 has an upper angled rear edge 257a that abuts with an angled forward edge 102a of the upper chassis of the housing. Similarly, the upstanding portion 255 comprises an upwardly oriented rear edge 255a that abuts with a corresponding forward edge 109a of the left side wall 109 of the lower chassis of the housing 100. Corresponding features will be provided on both sides of the apparatus. The abutment between those edges provides a stop to limit upward movement of the barrier 251 relative housing 100. When the barrier is in the covering position, the surfaces of the barrier are substantially contiguous with the surfaces of the housing. The upper finger contact regions 257 are aligned with the upper side surfaces 110a, 110b of the housing, as shown in FIG. 2.

The upper finger contact regions 257 on the upstanding portions 255 enable a user to actuate the guard 200 without putting their fingers close to the base flange 255 of the liquid chamber or the heater plate 140. The upper finger contact regions 257 on the upstanding portions 255 also enable a user to actuate the guard 200 without their fingers blocking the removal of the liquid chamber 151 from the recess 108.

In the configuration shown, each upstanding portion 255 comprises a narrow section 259 beneath the upper finger contact region 257 to accommodate the base flange 155 of the liquid chamber 153 when the guard is in the access position (shown in broken lines in FIG. 4). In an alternative configuration, the upstanding portions 255 could be more widely spaced apart than the widest dimension of the liquid chamber (i.e. of the base flange 155). In that configuration, the upstanding portions 255 may not comprise the narrow section. Instead, the liquid chamber 153 will simply be able to pass over the transversely extending body portion 253 of the barrier when the barrier 251 is in the access position.

At least part of the base 201 of the guard 200 is flexible. Said at least part of the base 201 is configured to flex as the barrier 251 is moved by a user between the covering position and the access position. Substantially the entire base 201 of the guard may be flexible, other than the regions of the fastener receiving apertures 203 such that the base 201 of the guard 200 can flex about the fastening locations. Alternatively, discrete portion(s) of the base 201 of the guard may be flexible with other discrete portion(s) of the base 201 of the guard being more rigid. For example, the first end 201a of the base may be substantially rigid, with one or more discrete transverse flexible strips being positioned between the first end 201a and the second end 201b, optionally with one or more discrete transverse relatively rigid strips being positioned between the transverse flexible strips.

FIG. 8 shows a configuration of the base 201 which has two spaced apart reduced thickness portions 202a extending in a forward-rearward direction of the guard 200 and positioned toward either side of the base 201. A transverse reduced thickness portion 202b extends between the two reduced thickness portions 202a adjacent the first end 201a of the base 201. Substantially the entire remainder of the base 200 comprises increased thickness portions 202c in regions where greater strength or resistance to bending is desired, for example, around the alignment aperture 211. The first end 201a of the base portion comprises a step 202d that extends across the first end and along a portion of each side of the base portion, to interact with a valve module housing 115a on the underside of the housing 100. Any other suitable configuration of reduced thickness portions, increased thickness portions, and/or steps could be provided.

The base 201 of the guard 200 is configured so that the barrier 251 can substantially only move up and down in two opposed directions as indicated by arrows UD in FIG. 4, by flexing the base 201 of the guard, and so that the barrier 251 cannot substantially move in other directions by flexing the base 201 of the guard 200, even if a single region of the barrier is pushed by a user. With that configuration, the guard cannot substantially twist about an axis extending in a forward-rearward direction of the breathing assistance apparatus (i.e. extending along the base 201 and through the barrier 251), to assist with minimising or preventing binding of the guard 200 during movement by a user. Because the guard 200 is on the outside of the housing 100, even if some twisting of the base 201 occurs, the guard 200 should not bind.

The barrier 251 may move any suitable distance in the opposed directions UD. For example, the barrier may move at least 5 mm, optionally up to 20 mm, optionally between 5 mm and 15 mm, optionally between 8 mm and 13 mm, or any other suitable distance.

An advantage of the guard 200 not twisting undesirably, is that a user can push on one side of the barrier 251 and pull the liquid chamber 151 out of recess 108 in the removal direction. If the guard 200 twisted, the liquid chamber 151 could be blocked on one side.

In order to be able to actuate the guard 200 by pressing on one side of the barrier 251, the guard 200 achieves the following two functions:

1. Pressing on one side of the barrier 251 (i.e. the upstanding portion 255) results in enough vertical movement in the section of the barrier that is blocking the chamber (i.e. the transverse portion 253), such that the barrier 251 is no longer blocking the liquid chamber 151.
2. Pressing on one side of the barrier (i.e. the upstanding portion 255) does not result in the guard 200 binding (and therefore limiting the range of motion of the barrier 251).

The following features enable function 1.

The substantial width of the base 201, combined with the base 201 being connected to the housing 100 at two spaced apart locations (i.e. adjacent both sides of the housing), minimises twisting of the base 201, so that the base only flexes about a first transverse axis. That is, the base 201 of the guard acts like a torsion bar, and allows flexing in the desirable directions UD, but resists twisting. As such, a downwards force placed at any location on the barrier 251 of the guard will cause the guard to flex downward evenly, instead of twisting and binding. Therefore, a user can actuate the guard 200 by pushing downwards on a single one of the upper finger contact regions 257.

Additionally, inner or rear surfaces 255a (FIG. 8) of the upstanding portions 255 interact with a support portion of the housing 100. In particular, the inner or rear surfaces 255a are substantially vertical surfaces that slide along complementary substantially vertical upright wall surfaces 112a (FIG. 15) that are provided on forwardly projecting extension members 112 on either side of the lower chassis 104. The sliding contact occurs for at least part of the movement of the guard.

Because the guard 200 does not twist, any vertical movement in one side of the barrier 251 would result in similar vertical movement throughout the rest of the barrier 251. If the barrier 251 did twist, then the amount of vertical movement would be reduced in sections of the barrier 251 that are distal to the side that the user is pressing. This reduced movement may not be enough to allow the liquid chamber 151 to be removed from the recess 108.

The guard 200 can also be structured such that the barrier 251 can be actuated further than is required to remove the liquid chamber 151 from the recess 108. In this configuration, a user could then press on a side of the barrier 251 and actuate guard 200 as far as possible. Even if there was a small amount of twisting, then the slightly reduced vertical movement in the transverse portion 253 would still be enough to allow the liquid chamber 151 to be removed from the recess 108.

The following features enable function 2.

For the guard 200 to bind, the barrier 251 would need to divert from its usual path while being actuated. When pressing on one side of the barrier 251, this would be caused by the base 201 twisting, such that the barrier 251 contacts part of the housing 100. The width of the base 201 combined with the spaced apart locations of the fasteners 205, and the surfaces 112a, 255a sliding past one another, limit the amount of twisting, such that this does not occur.

Figure 15:
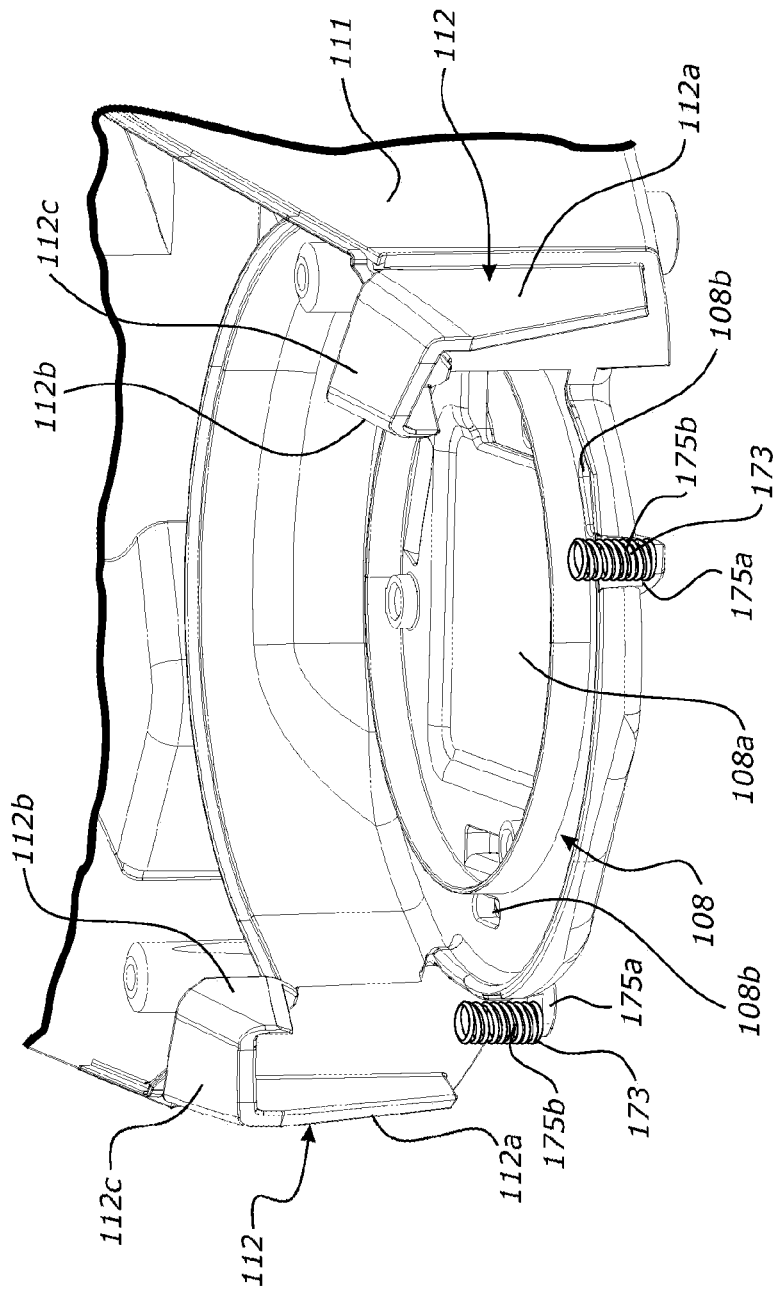
FIG. 15 is a part sectional perspective view of the base of the recess of the breathing assistance apparatus base unit with the heater plate removed, showing biasing device-receiving features and biasing devices.

Additionally, the shape of the housing 100 and guard 200 is designed to reduce the chance of binding occurring. As shown in FIG. 15, the housing 100 has extension members 112 that protrude from the front of the lower chassis 104. These extension members 112 are designed to contact the inner surface of the barrier 251 when in the covering position to help located the barrier 251 in the correct position. In particular, outer 112a, inner 112b, and upper 112c walls of the extensions 112 are configured to contact outer 255a, upper 255c, and inner 255b rear walls of the upstanding portions 255 of the barrier 251. Also shown in FIG. 15 is the taper of these extension members 112, where the forward parts of the extension members 112 are closer together than rearward parts of the extension members 112. The purpose of the taper is to allow for a close fit between the upstanding portions 255 of the barrier 251 and the extension members 112 when the barrier is in a covering position, creating a greater clearance between the upstanding portions 255 of the barrier and the extension members 112 as the guard 200 is actuated. This increased clearance reduces the chance of the guard 200 binding, even if there was a slight amount of twisting.

In an alternative configuration of the guard 200, the barrier 251 may comprise a single upstanding portion 255 at or adjacent a side of the transversely extending body portion, rather than two spaced apart upstanding portions 255. The barrier 251 will be movable by a user applying force to the upper finger contacting region 257 of the upstanding portion 255, between the raised covering position in which the barrier 251 partly covers the recess 108 and the lowered access position in which the recess 108 is less covered or is uncovered by the barrier. Said at least part of the base 201 that is flexible will be configured to flex as the barrier 251 is moved between the covering position and the access position. The single upstanding portion 255 may have any of the configurations described herein for the two upstanding portions. The housing may have a single one of the extension members 112. The opposite side of the transversely extending body portion 253 may be substantially coplanar with the upper wall 254d of the transversely extending portion 253 of the barrier 251, and may terminate shorter at the edge of the recess 108 corresponding to the opposite side of the liquid chamber 151 or may extend to the opposite side wall of the housing 100.

As discussed above, the breathing assistance apparatus may comprise a heater plate 140 in the recess 108. The recess 108 is configured to removably receive the liquid chamber 151. The guard 200 shields the base flange 155 and thereby the base 154 of the liquid chamber 151 from contact by a user when the barrier 251 of the guard 200 is in the covering position and when a liquid chamber 151 is in position in the recess 108.

During use, the heater plate 140 can reach high temperatures, which could cause harm to a user if they were to touch it or the base flange 155 of the liquid chamber close to the heater plate 140, such as while handling the breathing assistance apparatus or while connecting/disconnecting the humidifier liquid chamber 151 to/from the base unit 50 of the breathing assistance apparatus. The guard 200 minimises the likelihood of the user touching the heater plate 140 or base flange 155 of the liquid chamber 151.

Additionally, or alternatively, the recess 108 is configured to removably receive the liquid chamber 151. The barrier 251 blocks insertion or removal of the liquid chamber 151 into or from the recess 108, in the absence of flexing of the base 201 of the guard 200. As shown in FIG. 16, the upper edge 254d of the transversely extending portion 253 of the barrier is positioned to at least partly overlap the base flange 155 of the base 154 of the liquid chamber, so that the liquid chamber 151 cannot be moved in the removal direction RD without flexing the base 201 of the guard 200 so that the barrier 251 moves downward a sufficient distance to enable the liquid chamber 151 to be removed from the recess 108.

The base 201 of the guard 200 can be flexed by a user pushing on the barrier 251. The user can apply a downward force on the barrier 251 of the guard to move the barrier from the covering position to the access position.

In one configuration, the base 201 of the guard 200 can also be flexed by moving the liquid chamber 151 in the removal direction RD from the recess 108. Referring to FIG. 16, the barrier 251 is configured such that contact between the liquid chamber 151 and a contact surface which is provided by the downwardly and rearwardly angled rear wall portion 254e of the barrier 251 as the liquid chamber 151 is moved in the removal direction RD, moves the barrier 251 from the covering position to the access position.

Figure 21:
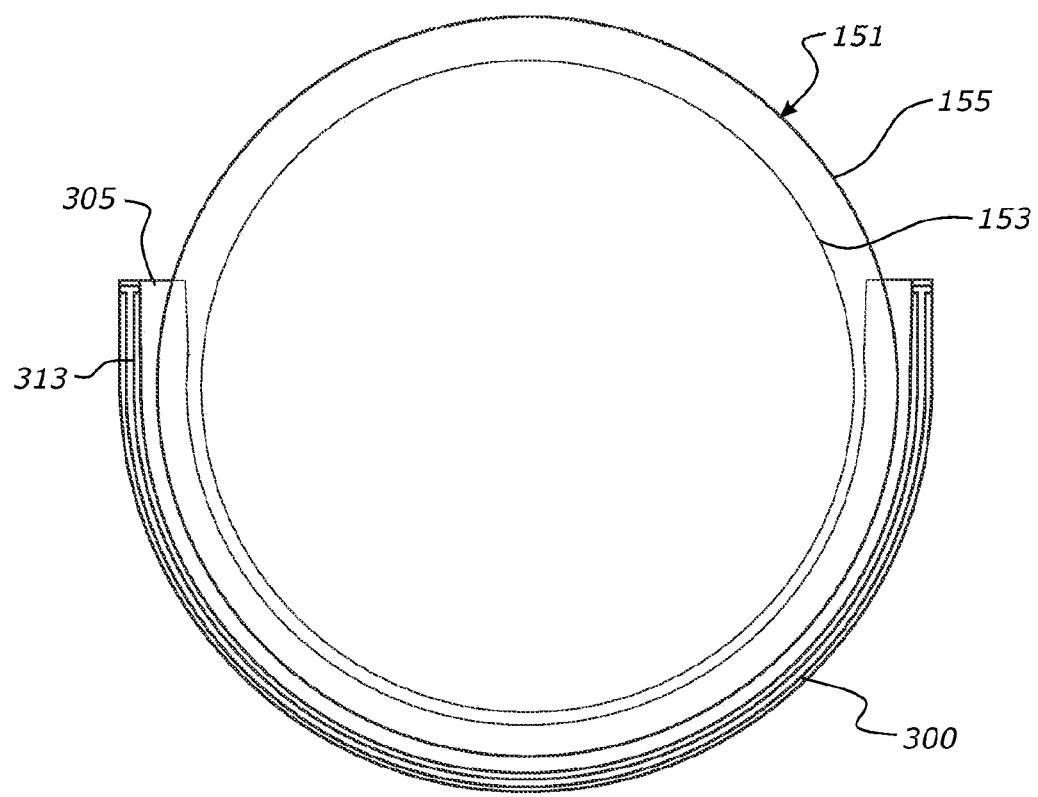
FIG. 21 is an underside view of the liquid chamber positioned with its base flange positioned under the liquid chamber retention rail.

In one configuration, the contact surface provided by the downwardly and rearwardly angled rear wall portion 254e is configured to contact substantially the entire front edge of the base flange (i.e. substantially the entire curved front edge of the base flange 155 that is visible in FIG. 2 and that is visible in front of the front edges of the guide rail 300 in FIG. 21) as the liquid chamber is moved in the removal direction.

By having the barrier 251 flex out of the way when the user attempts to pull out the liquid chamber 151, this allows the user to remove the liquid chamber 151 with one hand while keeping the other hand free to steady the base unit 50 of the breathing assistance apparatus 10. Additionally, by being able to pull out the liquid chamber 151 without directly interacting with the guard 200, the user is able to keep their hand further away from the heater plate 140, such that when the user is pulling out the liquid chamber 151 they are less likely to accidentally touch the temporarily exposed heater plate 140.

In the configuration shown, the liquid chamber 151 comprises a peripheral base flange 155 that extends outwardly from the bottom edge of the peripheral wall 153 of the liquid chamber, around the entire periphery of the liquid chamber. In that configuration, the base 154 of the liquid chamber, and more particularly the base flange 155, contacts the contact surface 254e of the barrier 251 as the liquid chamber 151 is moved in the removal direction RD, to move the barrier from the covering position to the access position.

In an alternative configuration of the liquid chamber 151, rather than having a peripheral base flange 155, two sides of the liquid chamber may comprise transverse projections that extends outwardly from the bottom edge of the peripheral wall 153 of the liquid chamber to engage with a liquid chamber retention guide rail 300 in the recess 108. The liquid chamber may not have projections extending in the removal direction RD or the opposite insertion direction ID. In that configuration, the wall 153 of the liquid chamber 151 and/or a forward edge of the base 154 beneath the wall of the liquid chamber contacts the contact surface 254e of the barrier as the liquid chamber is moved in the removal direction RD, to move the barrier 251 from the covering position to the access position. The barrier 251 will shield the base 154 of the liquid chamber from contact by a user when the barrier 251 is in the covering position and a liquid chamber is in the recess 108. With this configuration, the heater plate 140 may be more exposed to the front of the recess 108 than it would be with a liquid chamber 151 with a base flange 155. The barrier 251 may therefore also shield the heater plate 140 from contact by a user when the barrier 251 is in the covering position and a liquid chamber is in the recess 108.

The contact surface 254e of the barrier 251 that contacts the liquid chamber has an angled wall section. This means that when the user attempts to remove the liquid chamber 151, the horizontal movement of the liquid chamber in the removal direction RD results in a downwards force through the barrier 251 of the guard 200, thereby forcing the barrier 251 out of the way without further interaction between the user and the barrier 251.

Figure 17:
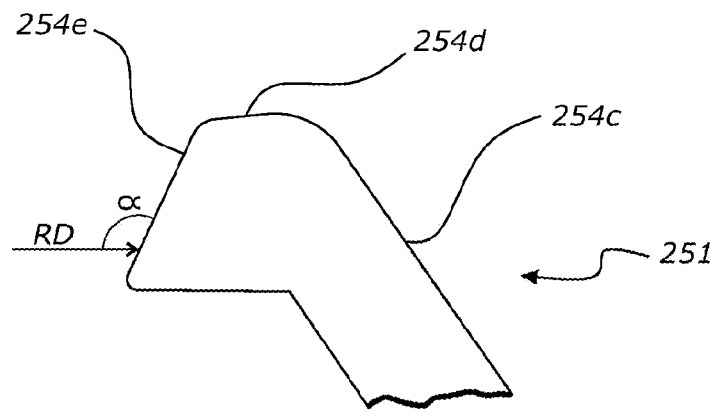
FIG. 17 is a schematic side view showing the angle a between the contact surface 24e of the barrier and the removal direction RD of the liquid chamber.

Referring to FIG. 17, the contact surface 254e of the barrier 251 is at a non-perpendicular angle a of more than 90 degrees and less than 180 degrees relative to the removal direction RD, optionally between 100 degrees and 170 degrees relative to the removal direction RD, optionally between 110 degrees and 135 degrees relative to the removal direction RD, optionally between 120 degrees and 130 degrees relative to the removal direction RD, and optionally 125 degrees relative to the removal direction RD. A flatter angle (i.e. closer to horizontal) allows for the liquid chamber's movement to more easily actuate the barrier 251, but means that the barrier needs to be longer to provide sufficient moment, so that the base unit 50 of the breathing assistance apparatus 10 takes up more space.

The contact surface 254e of the barrier 251 has a constant angle throughout a contact area between the liquid chamber and the contact surface, when viewed in side projection. This makes the liquid chamber 151 easier to pull out of the recess 108, because the liquid chamber 151 will always engage with the steepest angle of the contact surface 254e. The steepest angle determines the force required to pull the liquid chamber out of the recess 108.

In an alternative configuration, the barrier 251 is configured so that the base 201 of the guard 200 cannot be flexed by moving the liquid chamber 151 in the removal direction RD from the recess 108. The barrier 251 is configured such that contact between the liquid chamber and a contact surface of the barrier in a removal direction of the liquid chamber, will not cause the barrier 251 to move away from the covering position. In that configuration, the contact surface may be at an angle a of about 90 degrees or less relative to the removal direction RD of the liquid chamber.

If the angle is 90 degrees or less, the guard cannot be actuated by pulling the liquid chamber 151 from the recess 108 in the removal direction RD. If the angle is only slightly greater than 90 degrees, the force required to pull the liquid chamber 151 from the recess 108 may be unfeasibly high, depending on factors such as the biasing force of the guard and how hard a user can be expected to pull on the liquid chamber 151. Therefore, the barrier 251 will prevent the liquid chamber 151 being removed if the guard is unactuated by a user. To remove the liquid chamber 151, the user will need to push down on the barrier 251 to flex the base 201 so that the barrier no longer obstructs the liquid chamber 151 from being removed from the recess 108.

When the liquid chamber 151 is received in the recess 108, the base flange 155 (or the base 154 if there is no flange) of the liquid chamber may contact a surface of the barrier 251, such as the downwardly and rearwardly angled rear wall portion 254e. This functions to prevent movement of the liquid chamber 151 and to aid in retaining the liquid chamber 151 in connection with the ports 161, 163, in a configuration in which the guard cannot be actuated by moving the liquid chamber in the removal direction RD. Alternatively, there may be a small gap of about 0.5 mm for example between the base flange 155 and the barrier 251 when the liquid chamber is fully received in the recess 108.

Additionally, by having a tight fit between the barrier 251 and the liquid chamber 151 when assembled, the barrier 251 of the guard 200 would not return to its covering position unless the liquid chamber 151 is fully inserted. This may apply irrespective of the angle of the contact surface 254e. This indicates to a user that the liquid chamber is correctly connected once the barrier 251 of the guard 200 returns to its covering position. Having the liquid chamber 151 correctly connected is important as it ensures a pneumatic seal has been formed.

Before inserting/removing the liquid chamber, the user may press down on the guard 200 to flex the guard, such that the barrier 251 shifts out of the way. Alternatively, the guard may be designed such that the user does not necessarily need to do this. When inserting the liquid chamber 151, the user may begin by inserting the liquid chamber higher than the liquid chamber's final position, and/or at an angle to the housing 100 of the base unit 50 of the breathing assistance apparatus 10 (with the connecting side of the liquid chamber 151 angled downwards). As the liquid chamber 151 is inserted, the base flange 155 of the liquid chamber 151 would then push against the angled forward wall portion 254c or the rearwardly projecting upper wall portion 254d to push the barrier 251 of the guard toward the lowered access position. Once the liquid chamber 151 is fully inserted in the recess 108, the guard 200 will then flex so that the barrier 251 returns to the covering position such that the barrier 251 blocks the user from touching the base flange 155 of the liquid chamber. The barrier returning to the covering position can be used as an indication to the user that the liquid chamber 151 has been fully connected to the ports 161, 163 of the breathing assistance apparatus.

The guard 200 is configured so that the barrier 251 is biased to the covering position.

Figure 10:
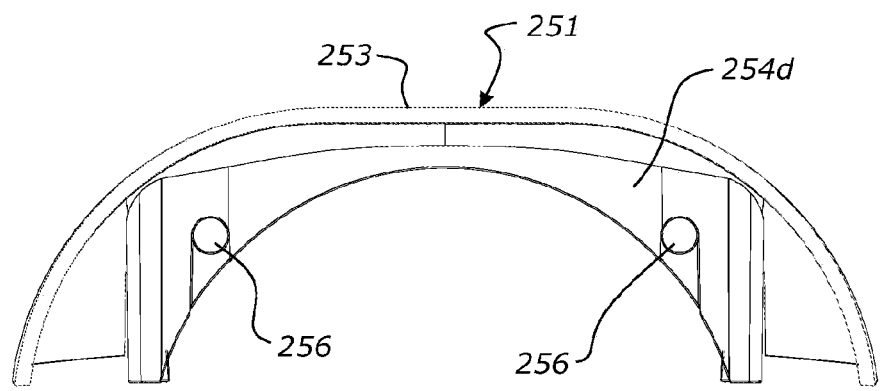
FIG. 10 is an underside view of the upper wall of the barrier of the guard, showing biasing device-receiving features.

In one configuration, one or more biasing devices act between the housing 100 and a portion of the guard 200 to bias the barrier 251 to the covering position. The biasing device(s) could be located anywhere between the housing 100 and the guard 200, such as between the housing 100 and the barrier 251 or the base 201 of the guard 200. The biasing device(s) may advantageously be positioned close to the front of the guard 200, as this will generate a greater moment across the guard 200. In the configuration shown, the biasing device(s) act between the housing 100 and the barrier 251, and in particular between the lower chassis 104 and the barrier 251. The biasing device(s) could have any suitable form, such as spring(s), resilient block(s) or member(s), or any other suitable configuration. FIGS. 10 and 15 show one exemplary configuration in which compression coil springs 173 provide a biasing force between the housing 100 and the barrier 251. In an alternative configuration, the springs could operate in tension, with the biasing force pulling the housing 100 and the guard 200 towards each other. The lower chassis of the housing comprises two spring mounts comprising radially extending base supports 175a and upstanding projections 175b that are positioned at or adjacent a forward end of the recess 108. The underside of an upper portion, such as the rearwardly projecting upper wall portion 254d, of the barrier 251 comprises two corresponding spring mounts 256 comprising recesses that receive upper ends of the springs 173. By providing recesses, the likelihood of the upper ends of the springs dislodging is minimised.

Any suitable number of biasing devices could be used, such as one, two, three, or more biasing devices. Because the base 201 of the guard 200 is substantially prevented from twisting during flexing, a single biasing device may be sufficient. The biasing device mounts could be modified depending on the types of biasing devices that are used.

When biasing device(s) is/are used, the base 201 of the guard may be flexible but not resiliently flexible, so that the base 201 does not provide a biasing force to the covering position.

Alternatively, or additionally, part of the guard 200 is resiliently flexible, to bias the barrier 251 to the covering position. In one configuration, said at least part of the base 201 of the guard 200 is resiliently flexible, to bias the barrier 251 to the covering position. That is, in some configurations, the barrier 251 may be biased to the covering position solely by the resilience of the base 201 of the guard, solely by one or more biasing devices, or by a combination of the biasing device(s) and the resilience of the base 201 of the guard 200.

By biasing the barrier 251 to the covering position, a basic force is provided that needs to be overcome for the user to begin actuating the guard 200. Additionally, this accounts for a small amount of deformation of the guard 200 that may occur throughout the life of the breathing assistance apparatus, thereby helping to ensure that the guard 200 still functions as intended by returning the barrier 251 to the correct covering position when unactuated.

As discussed above, the guard 200 is mounted to the exterior of the housing 100. An advantage of this is that a user can see the guard 200 from either side of the base unit 50 of the breathing assistance apparatus 10. This is beneficial because the colour of the guard may be used to identify the purpose or function of the apparatus, as described above. Alternatively, or additionally, the contact between the barrier 251 and the housing 100 may be used to determine if the liquid chamber 151 has been correctly/fully inserted into the recess 108 and connected to the ports 161, 163 of the apparatus 10.

Figure 26:
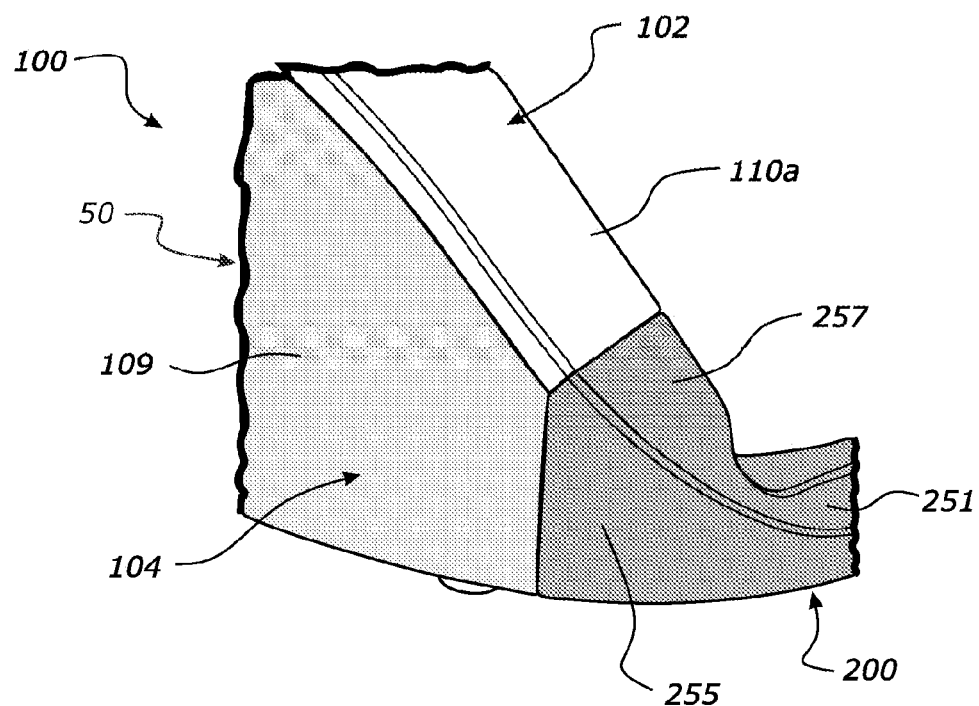
FIG. 26 is enlarged front/left side overhead perspective view of a forward region of the breathing assistance apparatus base unit, showing the barrier 251 in the covering position.
Figure 27:
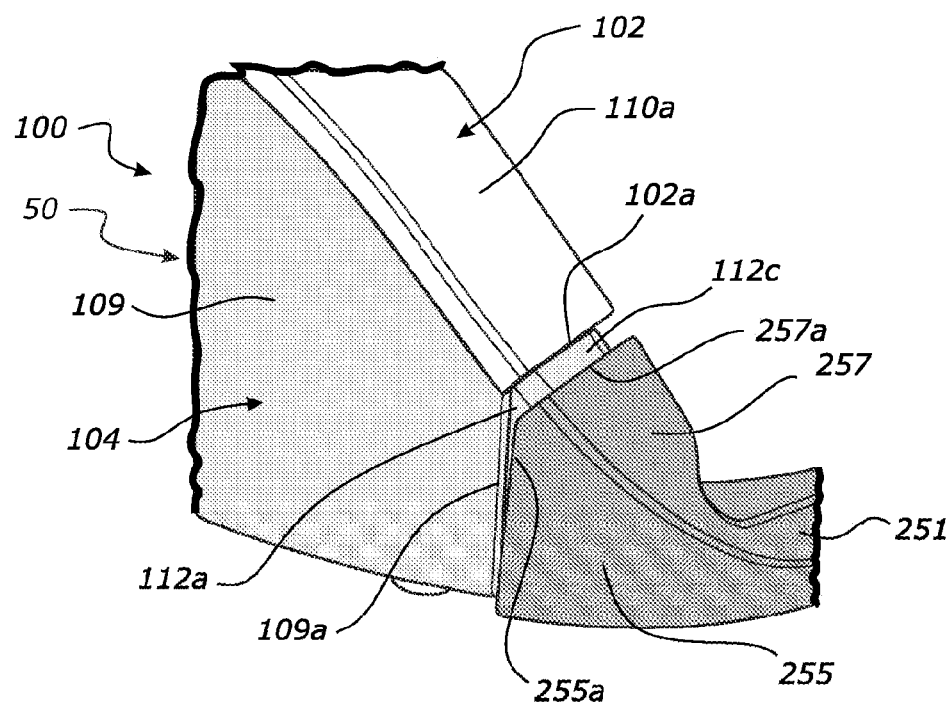
FIG. 27 is a view corresponding to FIG. 26 but with the barrier 251 in the access position.

An exemplary configuration of the base unit 50 having different surfaces with different colours, as described below, is shown in FIGS. 26 and 27.

The housing 100 comprises an outer surface such as surfaces 110a, 110b having a first colour. In some configurations, the entire upper chassis 102 may have the first colour. Alternatively, different regions of the upper chassis 102 may have different colours. A portion of the housing 100, such as one or more of the surfaces 112a, 112b, 112c of the extensions 112 (FIG. 15), has a second colour that differs from the first colour. In some configurations, the entire lower chassis 104 may have the second colour. Alternatively, different regions of the lower chassis 104 may have different colours.

The guard 200 has a colour that differs from the second colour of the extension members 112. In some configurations, the guard 200 has a third colour that differs from the first colour and the second colour. Alternatively, the guard may have a colour that is the same as the first colour, but that differs from the second colour.

The second colour will be chosen to be visually distinctive from the first colour and, if applicable, the third colour. For example, there may be a high contrast between the colours. Alternatively, or in addition, the second colour may be selected to be a colour that is typically associated with a warning; for example, red or orange.

The barrier 251 is configured to cover the portion 112 of the housing having the second colour when the barrier is in the covering position so that the portion having a second colour is not visible from an exterior of the apparatus 10. The barrier 251 is configured to expose the portion 112 having a second colour when the barrier 251 is not in the covering position, so that the portion having a second colour is visible from an exterior of the apparatus 10 when the barrier is not in the covering position.

The extension members 112 are positioned behind and/or below a portion of the barrier 251 when the barrier is in the covering position. In particular, the extension members 112 are positioned behind and/or below the upstanding portions 255 of the barrier 251 when the barrier is in the covering position, and the extension members 112 are exposed by the upstanding portions 255 when the barrier 251 is not in the covering position.

Similar colour features could be incorporated into an apparatus having a single upstanding portion 255 on the barrier 251 and a single extension member 112 on the housing, or into an apparatus that does not have upstanding portions on the barrier. For example, the barrier 251 may comprise a transverse cross-member 253 that exposes a coloured portion of the housing 100 when the barrier 251 is not in the covering position, and that covers the coloured portion of the housing 100 when the barrier is in the covering position.

With the described configuration, when the barrier 251 is in the covering position, surfaces 255a, 257a of the barrier will contact surfaces 109a, 102a of the housing 100, so the user can only see the first colour of the housing and the colour of the barrier 251 from above and/or from either side of apparatus. This serves as a visual indicator that the barrier 251 is in the covering position.

The second colour will be visible between the first colour of the housing and the barrier 251 from the exterior of the apparatus at any time the barrier 251 is not fully in the covering position. This serves as a visual indicator that the barrier 251 is not fully in the covering position. The second colour is visible from above and/or from either side of the apparatus, increasing the visibility of this feature.

The barrier 251 of the guard fully returning to its covering position indicates to the user that the liquid chamber 151 is fully connected to the ports 161, 163 of the apparatus. Therefore, whether or not the user can see the second colour from between the housing 100 and the guard 200 will provide an indication of whether or not the liquid chamber 151 is fully inserted and connected.

A liquid chamber retention guide rail 300, as shown in FIGS. 18-22, is provided in the recess 108. The guide rail 300 is fixed relative to the walls of the recess 108 so as to not move relative to the housing 100. When the liquid chamber 151 is inserted in the recess 108, its base flange 155 is positioned under the guide rail 300 to inhibit upward movement of the liquid chamber in the recess 108. The heater plate 140 may be biased upwards by one or more biasing devices, to apply upward force to the underside of the liquid chamber and so that the liquid chamber is held between the heater plate 140 and the guide rail 300.

The guide rail 300 is shaped as a semi-circular partial ring that complements the base flange 155 of the liquid chamber 151. The guide rail 300 is configured to extend around the back and sides of the recess 108, and around the back and sides of the base flange 155 of the liquid chamber 151, but is forwardly open to enable the liquid chamber to be inserted into the recess from the front, with the back and sides of its base flange 155 under the guide rail 300. The front edge of the base flange 155 of the liquid chamber 151 is exposed from the guide rail 300 when the liquid chamber 151 is positioned in the recess 108. The guide rail 300 counteracts the upwards force from the heater plate 140, and as such a guide rail that complements a large section of the liquid chamber is preferable as it distributes said load more evenly.

Figure 18:
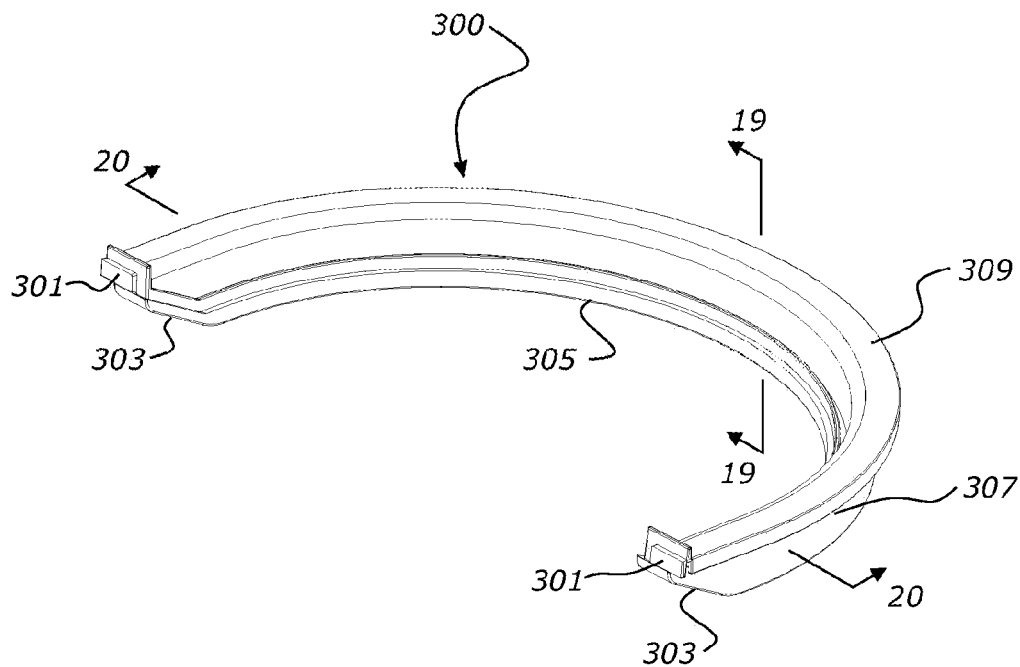
FIG. 18 is a front/right side overhead perspective view of the liquid chamber retention rail of the breathing assistance apparatus base unit.
Figure 19:
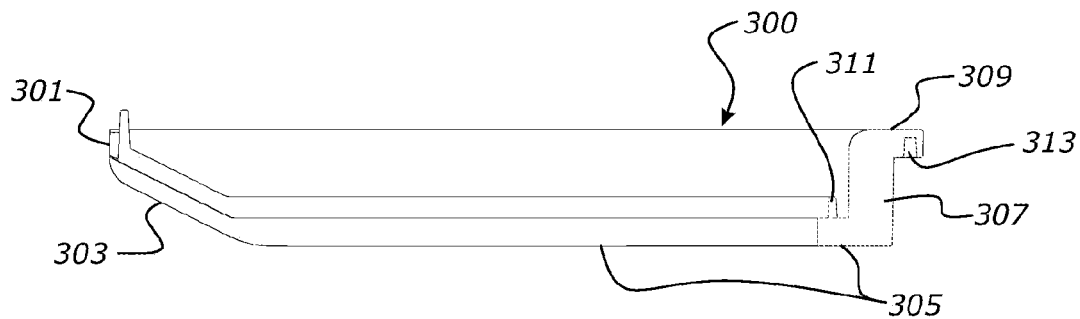
FIG. 19 is a sectional side view of the liquid chamber retention rail along line 19-19 of FIG. 18.

As shown in FIGS. 18 and 19, the underside of the guide rail comprises ramped sections 303 that extend downwardly and rearwardly from front edges 301 of the guide rail. The remainder of the underside comprises a flat section 305 that extends rearwardly from each ramped section 303 and around the back portion of the guide rail 300. The flat section 305 serves to contact the base flange 155 on the liquid chamber 151 when assembled and counteract the upwards force from the heater plate. The flat section 305 is parallel to the bottom of the liquid chamber 151 and/or with the upper surface of the heater plate 140, to enable the base flange 155 of the liquid chamber 151 to slide therebetween.

The ramped sections 303 aid in aligning the liquid chamber 151 as a user couples the liquid chamber 151 to the breathing assistance apparatus 10. For example, the ramped sections 303 would allow a user to insert the liquid chamber 151 from a height that is higher than the final position of the liquid chamber in the recess 108, and/or at a downwards angle. As the user pushes the liquid chamber 151 into the recess 108, the ramped sections 303 will direct the liquid chamber downwards until it contacts the heater plate 140 and/or the barrier 251. As the user continues to insert the liquid chamber 151, the liquid chamber will continue to be forced downwards by the ramped sections 303, thereby compressing the springs of the heater plate 140 and/or flexing the guard 200 such that the barrier 251 moves out of the way. Once the liquid chamber 151 reaches the flat section 305, the liquid chamber can then be pushed horizontally onto the ports 161, 163 of breathing assistance apparatus. Once the liquid chamber 151 is fully connected, the barrier 251 will no longer be contacting the bottom of the liquid chamber 151, and the barrier 251 will return to its covering position.

Figure 20:
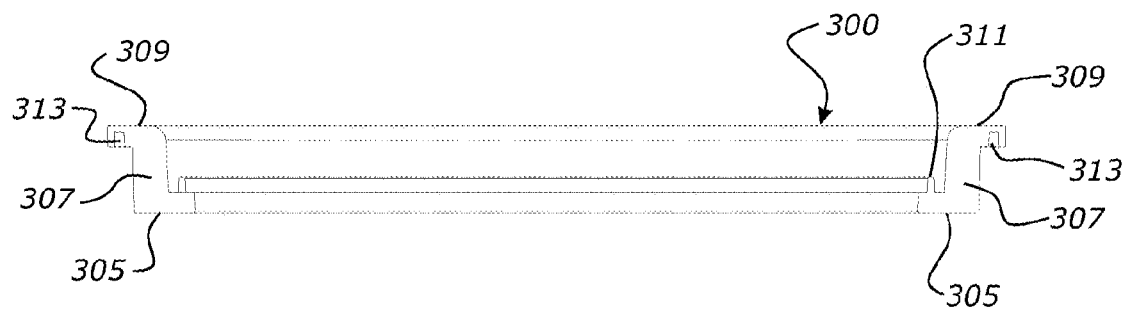
FIG. 20 is a sectional front view of the liquid chamber retention rail along line 20-20 of FIG. 18.

As shown in FIGS. 19 and 20, the guide rail 300 has a generally Z-shaped cross-sectional shape, comprising an upstanding wall portion 307, the flat base section 305 extending radially inwardly from a position at or adjacent the bottom of the upstanding wall portion 307, and an upper flange 309 extending radially outwardly from a position at or adjacent the top of the upstanding wall portion 307.

A first connection feature 311 is provided on or in an upper surface of the flat base section 305. A second connection feature 313 is provided on or in a lower surface of the upper flange 309. Either connection feature could take the form of a protrusion and/or recess, configured to engage with a complementary protrusion and/or recess on the housing 100 of the breathing assistance apparatus. The connection features may be substantially annular and extend substantially around the entire guide rail 300, or a plurality of discrete first connection features 311 and/or second connection features 313 could be provided. To provide the flat horizontal surface to contact the base flange 155 of the liquid chamber 151, the flat base section 305 of the ring extends radially inwards towards the centre of the ring, and the upper flange 309 extending radially outwards away from the centre of the ring.

Figure 22:
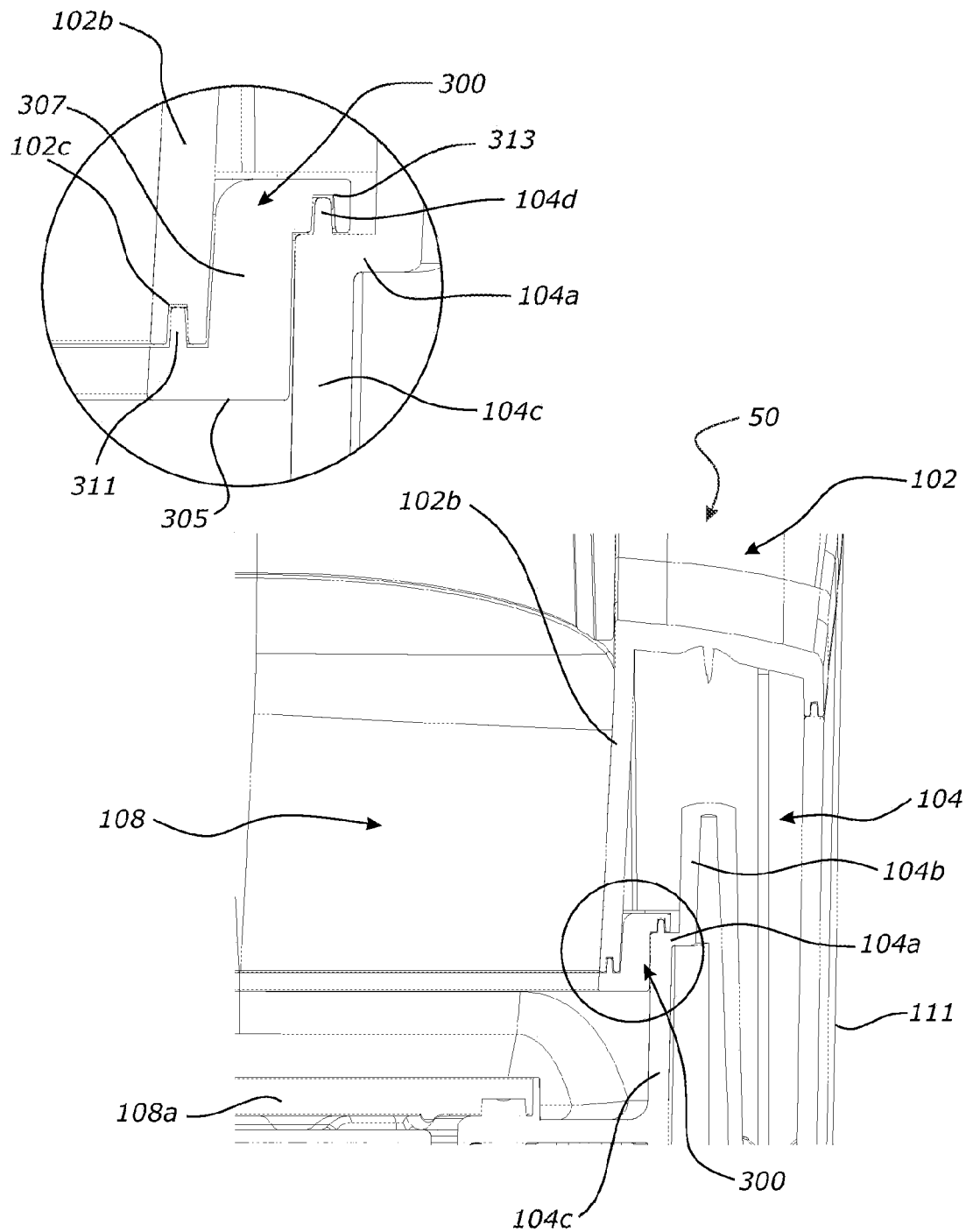
FIG. 22 is a sectional front view of the right side of the breathing assistance apparatus base unit showing the assembly of the liquid chamber retention rail with upper and lower chassis parts of the housing.

FIG. 22 shows the engagement between the guide rail 300 and the upper and lower chassis parts 102, 104 of the housing 100. The lower chassis 104 is configured to connect with the downwards facing connection feature 313 on the upper flange 309 of the ring. The upper chassis 102 is configured to connect with the upwards facing connection feature 311 on the flat base section 305 of the ring. When the upper and lower chassis 102, 104 are securely fastened together, the guide rail 300 is securely located relative to the housing 100 of the breathing assistance apparatus, without necessarily requiring any further adhesive or fasteners to secure it in place.

In the form shown, a bottom edge of a substantially vertical wall section 102b of the upper chassis 102 has a complimentary connection feature 102c to engage with the connection feature 309. An instep 104a between two wall portions 104b, 104c of the lower chassis 104 has a complementary connection feature 104d to engage with the connection feature 311. This configuration may extend around the sides and rear of the recess 108.

The substantially vertical wall section 102b of the upper chassis part 102 matches the shape of the innermost side of the upstanding wall portion 307 of the ring and the inner side of the inwardly extending flat base section 305. The edge of the ring and the substantially vertical wall section 102b of the upper chassis 102 form the upper section of the semi-circular liquid chamber recess 108. The diameter of this upper section of the liquid chamber recess 108 is smaller than the diameter of the base flange 155 of the liquid chamber 151. As such, if the user were to attempt to insert the liquid chamber 151 into the recess 108 with the base flange above the guide rail 300, the flange would contact the walls of the upper section, and the liquid chamber 151 would be blocked from being inserted. This prevents a user from incorrectly inserting the liquid chamber into the recess 108 with the base flange 155 above the guide rail 300, thereby making the insertion of the liquid chamber 151 more intuitive. Additionally, the diameter of the upper section of the recess 108 will be substantially wider than the diameter of the body of the liquid chamber 151, such that a user may be able to grip the sides of the liquid chamber when inserting/removing it to/from the recess 108.

The housing 100 of the base unit 50 of the breathing assistance apparatus 10 and/or the guard 200 comprise one or more drainage ports or drainage spaces 171 to allow liquid to drain through or around the base 201 of the guard 200. Any liquid that spills during connection/disconnection of the liquid chamber 151 would flow through the drainage port(s), instead of pooling near any electronics of the breathing assistance apparatus 10.

Figure 14:
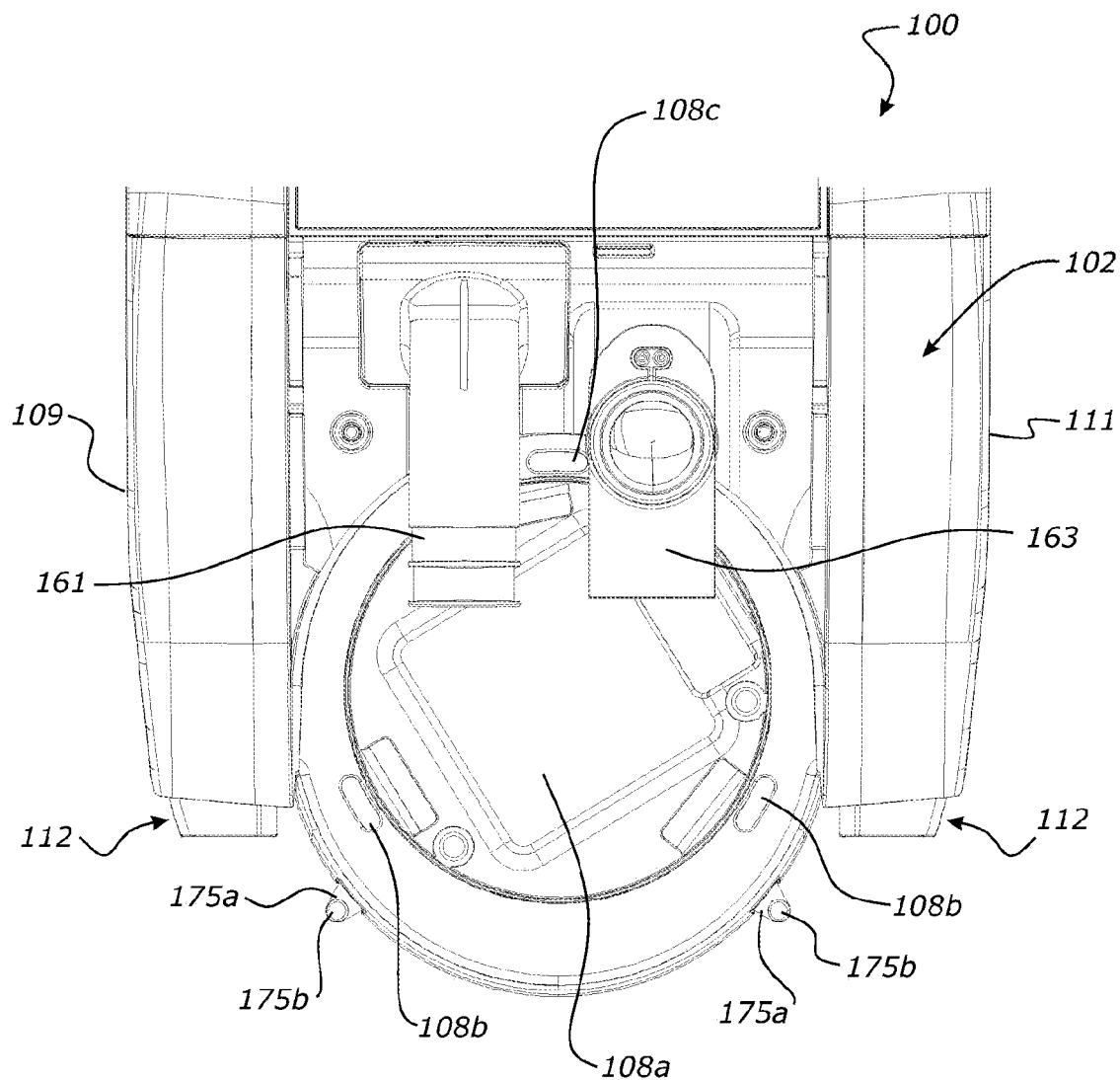
FIG. 14 is an overhead view of the recess of the breathing assistance apparatus base unit with the heater plate removed, showing drainage ports.

As shown in FIG. 14 for example, the base of the housing 100 may comprise forward/side drainage ports 108b and a rear drainage port 108c. The drainage ports are positioned near the heater plate 140. As mentioned earlier, a majority of the base 201 of the guard 200 may not contact the base of the housing 100, so once any liquid has flowed through the drainage ports 108b, 108c it should continue to drain out through the spaces 171 that are provided between the sides of the base portion 201 and the bottom wall 115 of the housing. Referring to FIG. 8, the guard 200 may comprise one or more drainage ports, such as drainage port(s) 254 in the lower wall portion 254a of the barrier, to assist with draining liquid. The drainage port(s) 254 in the lower wall portion will drain liquid when the barrier 251 is in the access position.

The housing 100 and/or guard could have any suitable configuration and/or number of drainage ports.

Figure 23:
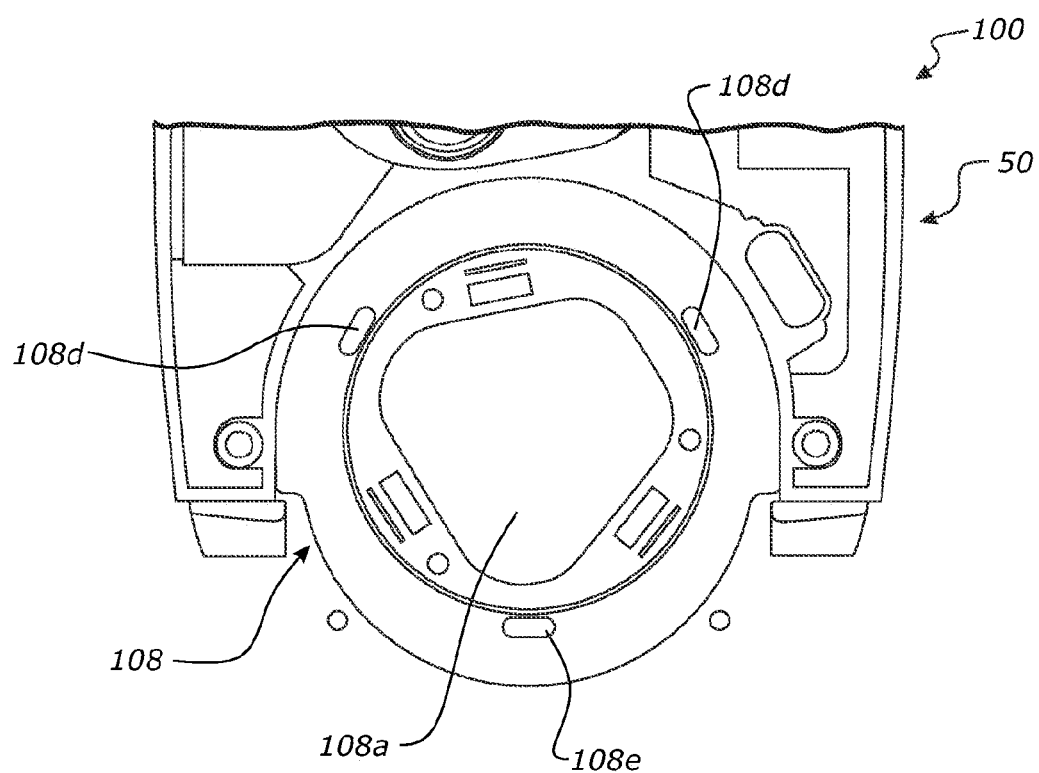
FIG. 23 is an overhead view of the recess of the breathing assistance apparatus base unit, showing alternative drainage ports.
Figure 24:
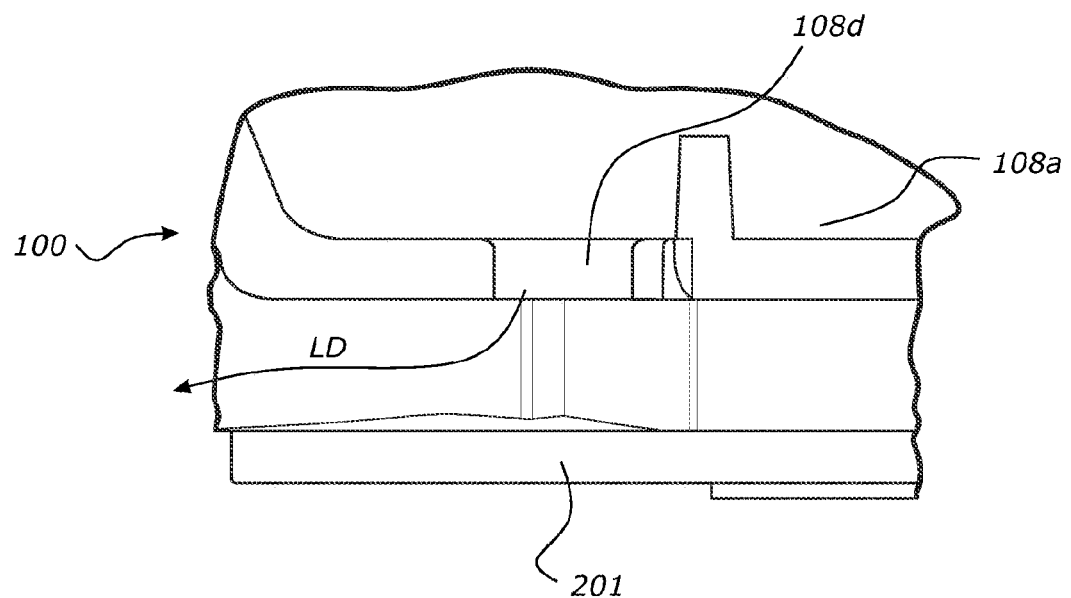
FIG. 24 is a part sectional front view of the breathing assistance apparatus base unit in the region of its side drainage ports.
Figure 25:
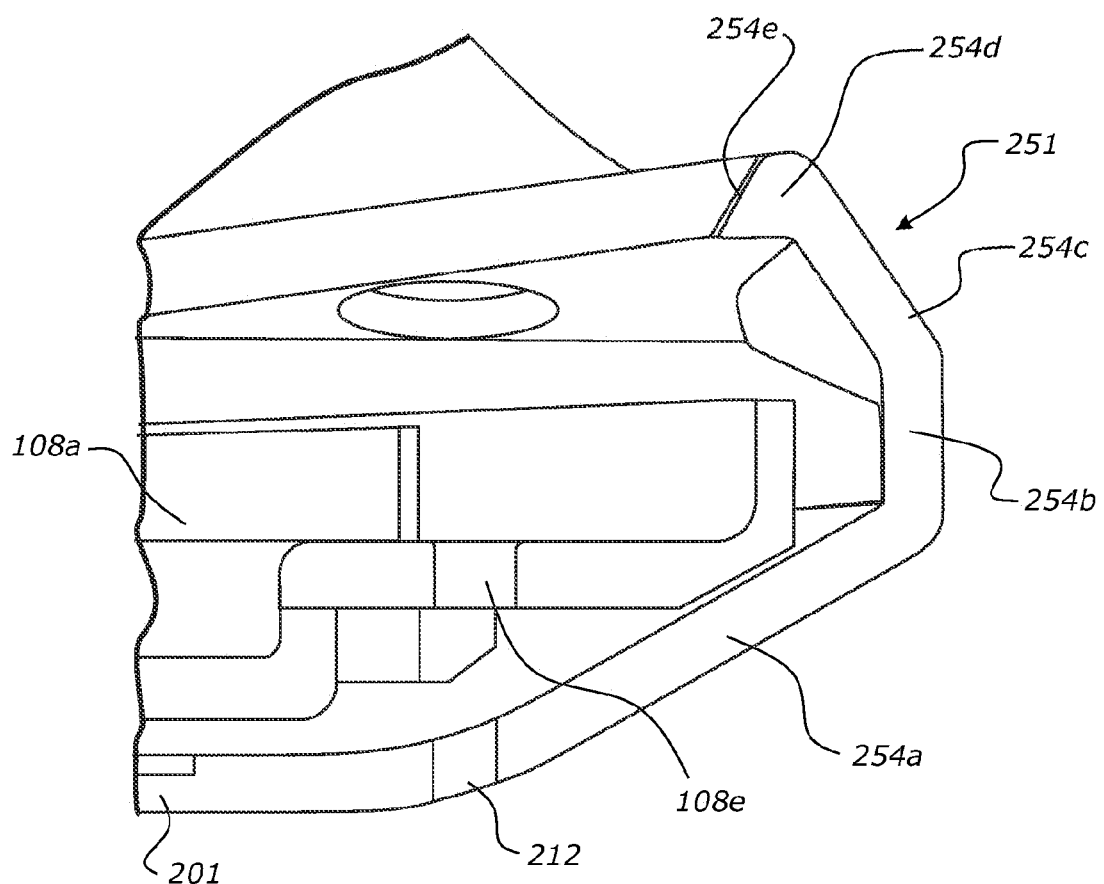
FIG. 25 is a partial sectional side view of the breathing assistance apparatus base unit in the region of its central drainage port.

FIGS. 23-25 show an alternative exemplary configuration. The base of the housing 100 comprises rearward/side drainage ports 108d and a forward central drainage port 108e. The drainage ports are positioned near the heater plate 140. Liquid that passes through the rearward/side drainage ports 108d can pass in direction LD though the space between the base 201 of the guard and the base of the housing 100.

As the forward central drainage port 108e is further from the edge of the base 201 of the guard 200 than the rearward/side drainage ports 108d, liquid that drains through this port 108e may not as easily continue to drain out around the edges of the base 201 of the guard 200 as it would for the rearward/side drainage ports 108e. As such, in this configuration the base 201 of the guard 200 has a drainage port 212. This drainage port 212 may be positioned substantially directly below the forward central drainage port 108e, such that any liquid that drains through the forward central drainage port 108e would continue to drain through the drainage port 212. The drainage port 212 could have any suitable shape, such as a shape similar to the alignment aperture 211 or a circular shape, for example. There may be a plurality of drainage ports 212 provided in the base 201 of the guard 200.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. Any one or more features from any of the configurations may be used in combination with any one or more features from any of the other configurations.

The features of the guard 200 are described with reference to a guard 200 having a base 201 at least part of which is flexible. Alternatively, one or more features of the guard 200 could be included in a guard that does not have a flexing base. For example, the angled contact surface 254e of the barrier 251 could be incorporated into a guard that does not have the flexible base 201. Instead, the angled contact surface 254e could be incorporated into a barrier of a guard that is linearly substantially vertically movable between the covering position and the access position, and that uses biasing device(s) to bias the barrier to the covering position. Such a configuration would still enable the barrier to be moved to the access position by moving the liquid chamber in the removal direction RD relative to the recess 108. However, the guard 200 with flexible base 201 is the preferred configuration, as it minimises the number of components. The configuration of the guard 200 with the flexible base 201 therefore provides simpler manufacturing and assembly, and also provides a compact region of the apparatus near the barrier 251 of the guard 200.

The guard 200 is described as a separate component that is connected to the housing 100 by fasteners. Alternatively, the guard 200 and/or housing could comprise integrated complementary coupling features, such as clips, to fasten the guard 200 the housing 100.

Alternatively, the guard 200 could be mounted to the housing by being an integral component of the housing 100. This could be done by having the base 201 extending from the lower chassis part 104 as a tab, with a cut out on each side of the base 201 allowing the guard 200 to flex relative to the rest of the housing 100. This configuration is less preferable as the entire lower chassis 104 would need to be replaced if the guard 200 was damaged.

The guard 200 is described with reference to a breathing assistance apparatus that can deliver heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the guard 200 may be used with an apparatus for a different purpose. The apparatus may be a high flow therapy apparatus, or may be a low flow therapy apparatus. For example, the features may be provided in an apparatus for providing continuous positive airway pressure (CPAP), which may deliver gases (humidified or otherwise) at lower flow rates, or may be provided in a medical insufflation apparatus.

The guard could be used in a standalone humidifier. The standalone humidifier may have a housing, a recess 108 for receipt of the liquid chamber 151, and a heater plate 140, but may not have a motor unit. The standalone humidifier may receive gases from an external source.

Accordingly, an alternative form breathing assistance apparatus 10 may be a standalone humidifier apparatus comprising a base unit 50 defining a main housing and a humidifier 12.

The standalone humidifier apparatus can deliver heated and humidified gases for various medical procedures, including respiratory therapy, laparoscopy, and the like. These apparatuses can be configured to control temperature and/or humidity. The apparatuses can also include medical circuits comprising various components that can be used to transport heated and/or humidified gases to and/or from patients. For example, in some breathing circuits, gases inhaled by a patient are delivered from a heater-humidifier through an inspiratory tube or conduit. As another example, tubes can deliver humidified gas (commonly $CO_2$) into the abdominal cavity in insufflation circuits. This can help prevent desiccation or 'drying out' of the patient's internal organs, and can decrease the amount of time needed for recovery from surgery. Heater wires may extend inside of at least a portion of the tubing forming the circuit to prevent or at least reduce the likelihood of the formation of significant condensation.

A standalone humidifier apparatus would typically include a base unit 50 and a humidifier liquid chamber 151. The base unit 50 can comprise a heater plate 140. The liquid chamber 151 can be configured to hold a volume of a liquid, such as water. The heater plate can be configured to heat the volume of liquid held within the liquid chamber 151 to produce vapour.

The liquid chamber 151 is removable from the base unit to allow the liquid chamber to be more readily sterilized or disposed, or to re-fill the chamber with liquid. The body of the liquid chamber 151 can be formed from a non-conductive glass or plastics material but the liquid chamber can also include conductive components. For instance, the liquid chamber can include a highly heat-conductive base (for example, an aluminum base) contacting or associated with the heater plate on the heater base.

The base unit can also include electronic controls such as a master controller. In response to user-set humidity or temperature values input via a user interface and other inputs, the master controller determines when (or to what level) to energize the heater plate 140 to heat the liquid within the liquid chamber 151.

The standalone humidifier apparatus can include a flow generator to deliver gases to the liquid chamber. In some configurations, the flow generator can comprise a ventilator, blower, or any other suitable source of pressurized gases suitable for breathing or use in medical procedures. The flow generator may be positioned in the base unit 50.

Alternatively, the standalone humidifier apparatus may comprise just the base unit 50 and the liquid chamber 151, and may be used with a separate or remote flow generator. The base unit 50 may be configured to fluidly connect to the separate or remote flow generator.

Therefore, the flow generator that is used with a standalone humidifier apparatus may be a wall gases source, ventilator, blower, or gas tank for example.

A standalone humidifier apparatus can be used with breathing therapies, positive pressure apparatus, noninvasive ventilation, surgical procedures including but not limited to laparoscopy, and the like. Desirably, the humidifier apparatus can be adapted to supply humidity or vapour to a supply of gases. The humidifier apparatus can be used with continuous, variable, or bi-level PAP systems or other form of respiratory therapy. In some configurations, the humidifier apparatus can be integrated into a system that delivers any such types of therapy.

An exemplary standalone humidifier apparatus is described in WO 2015/038013. The contents of that specification are incorporated herein in their entirety by way of reference.

The standalone humidifier apparatus may have any one or more of the features described or shown herein.

The guard could be used in an apparatus having a differently shaped liquid chamber, and the barrier of the guard could have its shape modified accordingly.

Reference to any prior art in this specification is not, and should not be taken as, an acknowledgment or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to when the apparatus is in a typical in-use position and/or with reference to particular orientations shown in the figures, and are used to show and/or describe relative directions or orientations.

The invention claimed is:

1. A breathing assistance apparatus comprising:
a housing with a recess configured to removably receive a liquid chamber;
a guard comprising a barrier, the barrier being movable between a covering position in which the barrier partly covers the recess and overlaps part of the liquid chamber when the liquid chamber is in the recess, and an access position in which the recess is less covered or is uncovered by the barrier and the barrier exposes the part of the liquid chamber when the liquid chamber is in the recess, wherein the barrier is biased to the covering position, and wherein the barrier is configured to move from the covering position to the access position by moving the liquid chamber in a removal direction from the recess;
wherein at least part of a base of the guard is flexible, wherein said at least part of the base is configured to flex as the guard moves; and
wherein the at least part of the base of the guard is configured so that the barrier can only move in two opposed directions by flexing the at least part of the base of the guard, and so that the barrier cannot move in other directions by flexing the at least part of the base of the guard even if a single region of the barrier is pushed by a user.

2. The breathing assistance apparatus according to claim 1, wherein the barrier is configured such that contact between the liquid chamber and a contact surface of the barrier as the liquid chamber is moved in the removal direction, moves the barrier from the covering position to the access position.

3. The breathing assistance apparatus according to claim 2, wherein the contact surface of the barrier is at a non-perpendicular angle of more than 90 degrees and less than 180 degrees relative to the removal direction.

4. The breathing assistance apparatus according to claim 2, wherein said part of the liquid chamber comprises a front edge of a base flange of the liquid chamber, and wherein the contact surface is configured to contact the front edge of the base flange as the liquid chamber is moved in the removal direction.

5. The breathing assistance apparatus according to claim 4, wherein the recess comprises a liquid chamber retention guide rail, and wherein the liquid chamber retention guide rail is forwardly open to enable the liquid chamber to be inserted into the recess with a back and sides of the base flange under the liquid chamber retention guide rail and with the front edge of the base flange exposed from the liquid chamber retention guide rail.

6. The breathing assistance apparatus according to claim 2, wherein the contact surface has a constant angle throughout a contact area between the liquid chamber and the barrier, when viewed in side projection.

7. The breathing assistance apparatus according to claim 1, wherein one or more biasing devices act between the housing and the guard to bias the barrier to the covering position.

8. The breathing assistance apparatus according to claim 7, wherein the one or more biasing devices act between the housing and the barrier.

9. The breathing assistance apparatus according to claim 7, wherein the barrier is linearly movable between the covering position and the access position.

10. The breathing assistance apparatus according to claim 1, wherein the at least part of the base of the guard is resiliently flexible and configured to bias the barrier to the covering position.

11. The breathing assistance apparatus according to claim 1, wherein the guard is integrally formed with the housing or is fastened to the housing.

12. The breathing assistance apparatus according to claim 1, wherein the barrier of the guard extends from the base of the guard at a location that is distal to a mounting of the base of the guard to the housing.

13. The breathing assistance apparatus according to claim 12, wherein the barrier of the guard extends upwardly from a position at or adjacent to a forward end of the base of the guard so as to be located at a front of the base.

14. The breathing assistance apparatus according to claim 12, wherein the housing comprises a projection and the base of the guard comprises a complementary aperture to receive the projection to resist horizontal movement of the base of the guard.

15. The breathing assistance apparatus according to claim 14, configured such that when the liquid chamber is removed from the recess, contact between the liquid chamber and the barrier applies force to the guard in a horizontal direction, and wherein the horizontal movement is prevented by the projection contacting a peripheral wall of the complementary aperture.

16. The breathing assistance apparatus according to claim 1, wherein the guard is configured so that it cannot twist about an axis that extends in a forward-rearward direction along the base and through the barrier of the guard.

17. The breathing assistance apparatus according to claim 1, further comprising a heater plate in the recess, wherein the recess is configured to removably receive the liquid chamber, and wherein the guard shields a base of the liquid chamber from contact by a user when the barrier is in the covering position and the liquid chamber is in the recess.

18. The breathing assistance apparatus according to claim 1, wherein the barrier blocks insertion or removal of the liquid chamber into or from the recess in the absence of flexing of the at least part of the base of the guard.

* * * * *